United States Patent
Jeanmaire et al.

(10) Patent No.: US 12,059,280 B2
(45) Date of Patent: Aug. 13, 2024

(54) METHODS AND SYSTEMS FOR DYNAMIC COLLIMATION

(71) Applicant: GE Precision Healthcare LLC, Milwaukee, WI (US)

(72) Inventors: Marion Jeanmaire, Malakoff (FR); Jorge Corsino Espino, Paris (FR); Veronique Felix, Gif-sur-Yvette (FR); Karima Santi, Maurepas (FR); Aurora Talaverano Fuentes, Madrid (ES); Fanny Patoureaux, Beynes (FR)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 627 days.

(21) Appl. No.: 16/801,050

(22) Filed: Feb. 25, 2020

(65) Prior Publication Data

US 2021/0259648 A1 Aug. 26, 2021

(51) Int. Cl.
*A61B 6/06* (2006.01)
*A61B 6/00* (2024.01)
(Continued)

(52) U.S. Cl.
CPC .............. *A61B 6/06* (2013.01); *A61B 6/025* (2013.01); *A61B 6/0414* (2013.01); *A61B 6/463* (2013.01);
(Continued)

(58) Field of Classification Search
CPC ......... A61B 6/06; A61B 6/025; A61B 6/0414; A61B 6/463; A61B 6/469; A61B 6/502;
(Continued)

(56) References Cited

U.S. PATENT DOCUMENTS

| | | | |
|---|---|---|---|
| 5,594,769 A | * | 1/1997 | Pellegrino .............. A61B 90/17 378/208 |
| 5,627,869 A | | 5/1997 | Andrew et al. |

(Continued)

FOREIGN PATENT DOCUMENTS

| | | |
|---|---|---|
| EP | 3143936 | 3/2017 |
| FR | 2956969 | 9/2011 |

(Continued)

OTHER PUBLICATIONS

EP application 21156124.6 filed 09FEB2021—Extended Search Report issued Jul. 26, 2021; 9 pages.
(Continued)

*Primary Examiner* — Sean D Mattson
(74) *Attorney, Agent, or Firm* — McCoy Russell LLP

(57) ABSTRACT

Methods and systems are provided for dynamic collimation adjustment during various x-ray imaging and image-guided procedures. In one example, collimation for an x-ray mammography system is adjusted based on a volume of interest, and further based on a workflow step of an imaging procedure. As an example, prior to a target selection, collimation may be adjusted to irradiate a larger volume of interest and x-ray system acquisition parameters, and hence, a greater area of a detector is irradiated; and after target coordinates are selected (e.g., for an interventional procedure), collimation may be adjusted to irradiate a reduced volume of interest based on the selected target and x-ray system acquisition parameters, and hence, a smaller area of detector is irradiated.

19 Claims, 13 Drawing Sheets

(51) Int. Cl.
*A61B 6/02* (2006.01)
*A61B 6/04* (2006.01)
*A61B 6/46* (2024.01)
*A61B 6/50* (2024.01)
*A61B 10/02* (2006.01)
*A61B 17/34* (2006.01)
*G06T 7/00* (2017.01)
*G06T 11/00* (2006.01)

(52) U.S. Cl.
CPC .............. *A61B 6/469* (2013.01); *A61B 6/502* (2013.01); *A61B 6/5294* (2013.01); *A61B 10/0233* (2013.01); *A61B 17/3403* (2013.01); *G06T 7/0016* (2013.01); *G06T 11/005* (2013.01); *G06T 2207/10081* (2013.01); *G06T 2207/10112* (2013.01); *G06T 2207/30068* (2013.01)

(58) Field of Classification Search
CPC ..... A61B 6/5294; A61B 6/482; A61B 6/5235; A61B 10/0233; A61B 17/3403; G06T 7/0016; G06T 11/005; G06T 2207/1008; G06T 2207/10112; G06T 2207/30068
See application file for complete search history.

(56) References Cited

U.S. PATENT DOCUMENTS

| | | | | |
|---|---|---|---|---|
| 5,970,112 A | * | 10/1999 | Hsieh | G21K 1/04 378/8 |
| 6,751,285 B2 | * | 6/2004 | Eberhard | A61B 6/544 378/37 |
| 7,120,224 B2 | * | 10/2006 | Gutman | A61B 6/4429 378/147 |
| 8,942,782 B2 | | 1/2015 | Sakaguchi | |
| 9,414,801 B2 | | 8/2016 | Kim et al. | |
| 9,931,087 B2 | | 4/2018 | Melman et al. | |
| 2010/0054395 A1 | * | 3/2010 | Noshi | A61B 6/032 378/16 |
| 2010/0091937 A1 | * | 4/2010 | Raupach | A61B 6/4035 378/150 |
| 2010/0091940 A1 | * | 4/2010 | Ludwig | A61B 6/4028 378/22 |
| 2010/0252740 A1 | | 10/2010 | Akahori | |
| 2011/0058645 A1 | * | 3/2011 | Heuscher | A61B 6/035 378/16 |
| 2012/0051498 A1 | * | 3/2012 | Koishi | A61B 6/5205 378/10 |
| 2015/0374314 A1 | * | 12/2015 | Maack | A61B 6/4405 378/151 |
| 2016/0310215 A1 | * | 10/2016 | Palma | A61B 90/39 |

FOREIGN PATENT DOCUMENTS

| | | | | |
|---|---|---|---|---|
| FR | 2956969 A1 | * | 9/2011 | ............. A61B 6/025 |
| JP | 2010239997 A | | 10/2010 | |

OTHER PUBLICATIONS

FR2956969—English translation of Abstract, 1 page; Espacenet.com [retrieved Sep. 13, 2021].

JP application 2021-019620 filed Feb. 10, 2021—Office Action issued May 11, 2022, Machine Translation, 5 pages.

JP patent application 2021-019620 filed Feb. 10, 2021—office action issued Nov. 30, 2022, Machine Translation, 4 pages.

* cited by examiner

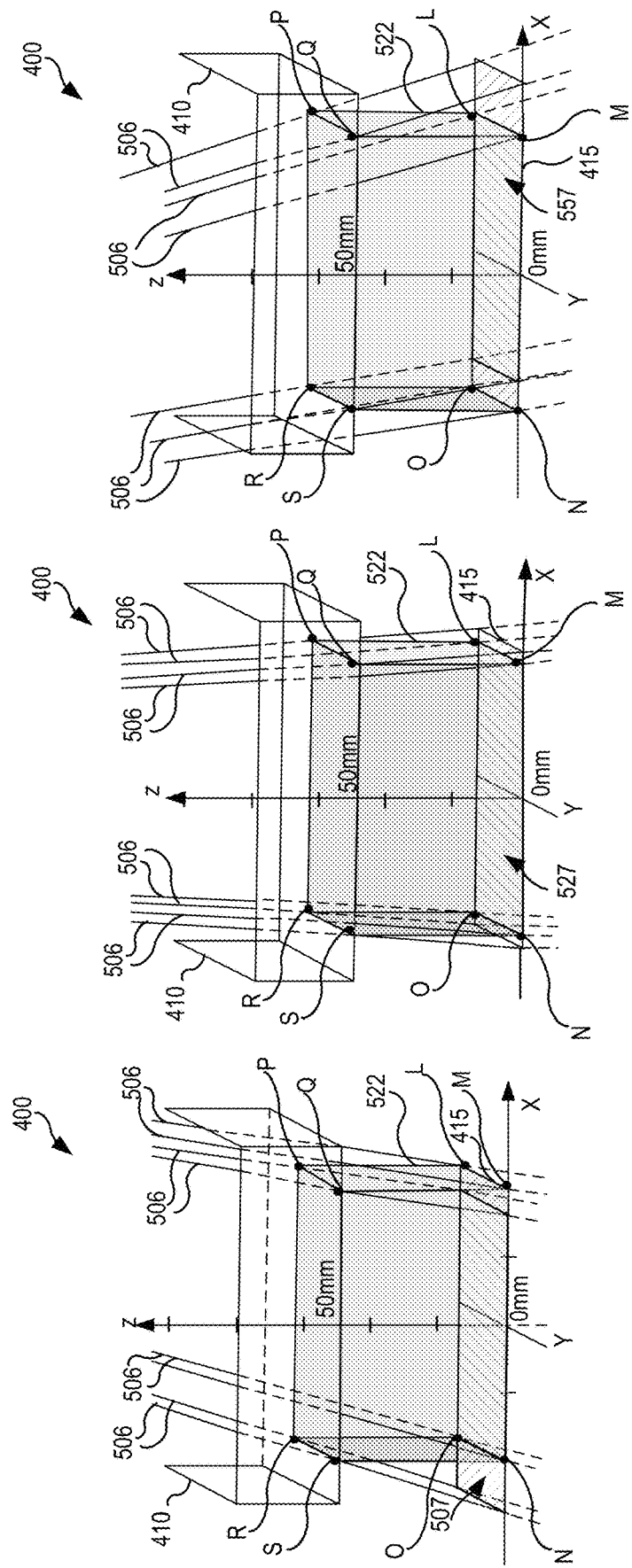

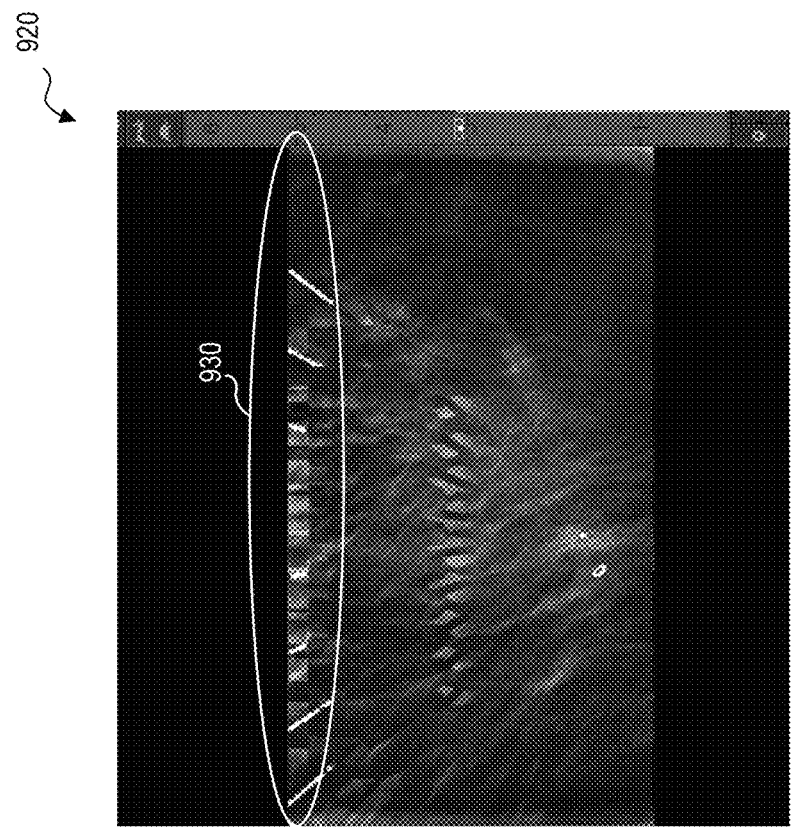
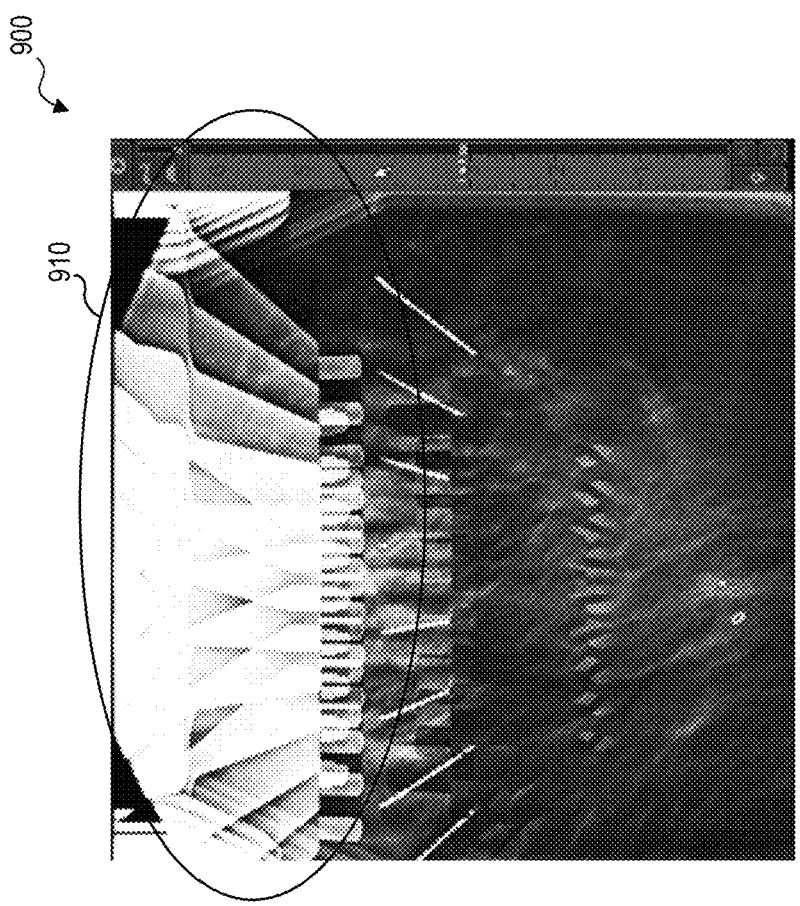
FIG. 9

METHODS AND SYSTEMS FOR DYNAMIC COLLIMATION

FIELD

Embodiments of the subject matter disclosed herein relate to x-ray mammography systems, and more particularly, to dynamic collimator adjustment during mammography and biopsy procedures performed with x-ray mammography systems.

BACKGROUND

Mammography is an x-ray imaging procedure for detecting one or more tumors of a breast. Based on mammography imaging, a breast biopsy procedure may be performed to obtain a biopsy sample of the concerned breast tissue for further analysis. Both mammography and biopsy procedures may be performed using an x-ray mammography system. Prior to imaging with the mammography system, the breast is compressed between a compression plate and detector. Radiation from an x-ray source is then directed towards the compressed breast and projection images are obtained at the detector. The projection images are reconstructed via image processing to obtain x-ray mammography images. When mammography is used for routine screening, each breast is imaged at two different views, particularly craniocaudal (CC) view and mediolateral oblique (MLO) view. In addition to mammography imaging, the x-ray mammography system may be utilized to perform a digital breast tomosynthesis (DBT) procedure where the compressed breast is scanned at various angles and a plurality of cross-sectional images are reconstructed. DBT may also be used for screening purposes to obtain a more clear view of the breast tissue. Additionally, diagnostic imaging may be performed when needed with the x-ray mammography system, wherein additional images of the concerned area, either by mammography or DBT, are obtained to detect abnormalities and assess initial diagnosis. DBT images may also be used for interventional procedures, such as a DBT guided biopsy procedure. Furthermore, follow-up imaging procedures, such as contrast enhanced spectral mammography (CESM), may be performed with the x-ray mammography system to evaluate progression of a disease in response to a treatment.

The x-ray mammography system may include a collimator to adjust an area irradiated by the x-ray radiation rays on the detector. Typically, the area to irradiate may be determined based on compression paddle dimensions, breast support, the type of application (e.g., DBT versus CESM)), and user selected settings.

BRIEF DESCRIPTION

In one embodiment, a method for an x-ray system, comprises: during an imaging procedure performed with the x-ray system, adjusting collimation to image a corresponding volume of interest based on a workflow step of the imaging procedure. In this way, by adjusting collimation to irradiate the volume of interest based on the workflow step, an amount of irradiation may be adjusted based on the imaging needs. As a result, artifacts visible in the image may be reduced. Further, by focusing on the imaging needs of the workflow step, faster image reconstruction may be achieved with reduced radiation exposure to the patient. Consequently, imaging quality and efficiency may be increased, and patient care may be improved.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIGS. 5A, 5B, and 5C show another exemplary three-dimensional illustration of dynamic collimation, including respective areas of irradiation at three different x-ray source angular positions, according to an embodiment of the disclosure;

FIG. 9 shows a set of exemplary mammograms illustrating reduction in imaging artifact due to dynamic collimation performed, according to an embodiment of the disclosure.

DETAILED DESCRIPTION

Figure 1A:
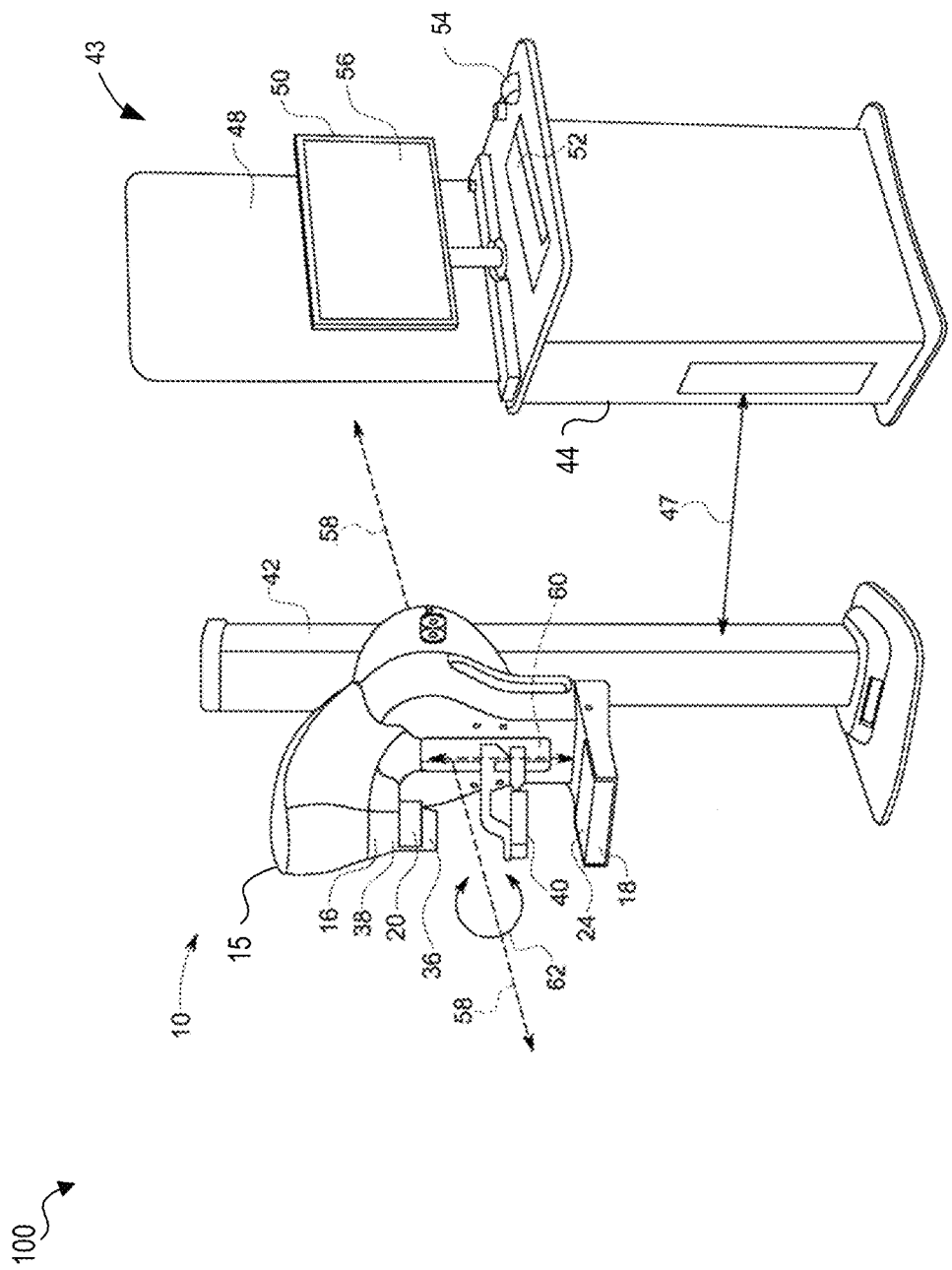
FIG. 1A is a schematic illustration of a mammography system for performing one or more imaging procedures, according to an embodiment of the disclosure.
Figure 1B:
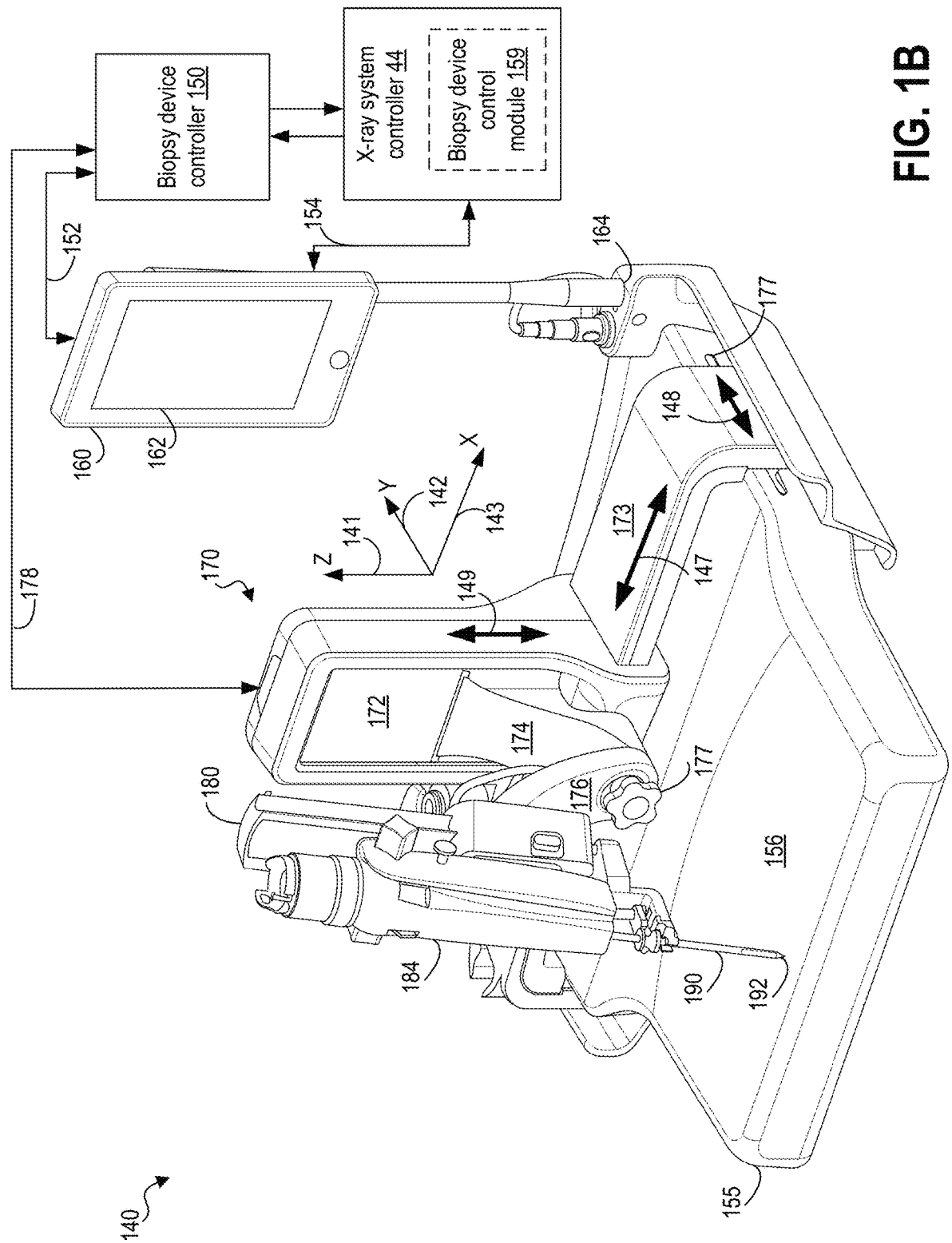
FIG. 1B is schematic illustration of a biopsy device that may be used in conjunction with the mammography system of FIG. 1A, according to an embodiment of the disclosure.

The following description relates to various embodiments for collimation in x-ray mammography systems, such as a mammography system described at FIG. 1A. The x-ray mammography systems may be utilized to perform digital mammography, digital breast tomosynthesis (DBT), contrast enhanced spectral mammography (CESM), and interventional procedures, such as stereo-guided biopsy, CESM-guided biopsy and DBT-guided biopsy. An exemplary biopsy device is shown at FIG. 1B. During any mammography procedure, the breast is compressed with a compression paddle in order to position the breast for imaging. During imaging with the x-ray mammography system, radiation from an x-ray source is directed to an imaging volume that includes the compressed breast, and projection images of the breast are obtained at the detector. X-ray mammography systems include a collimator to adjust field of view of x-ray systems and thereby adjust an irradiated portion of the compressed breast. Thus, an amount of irradiation that the patient is exposed is based on the collimation performed with the collimator. Further, imaging requirements may vary during a procedure.

Figure 2A:
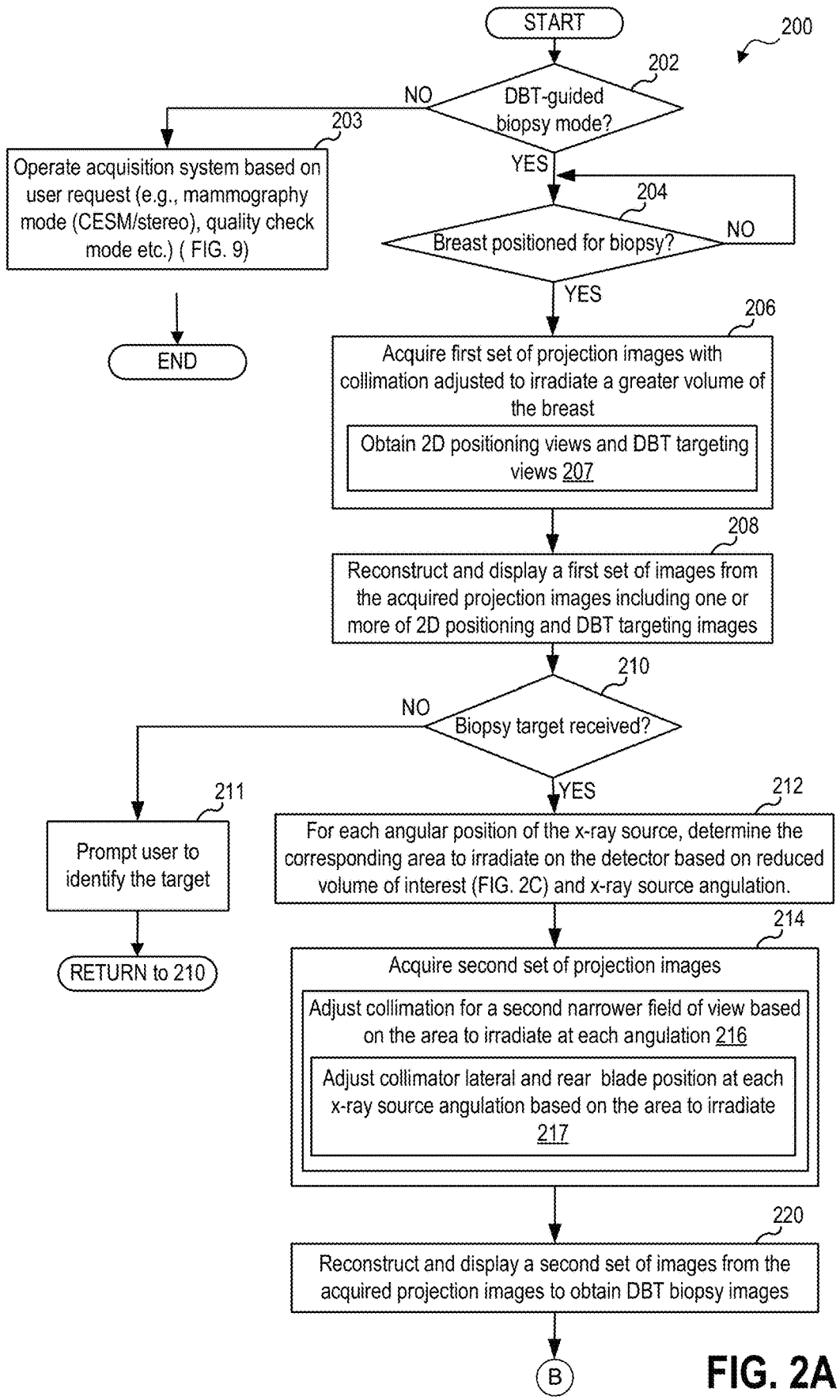
FIG. 2A is a high-level flow chart illustrating a method for collimation during a DBT guided biopsy procedure, according to an embodiment of the disclosure.
Figure 2B:
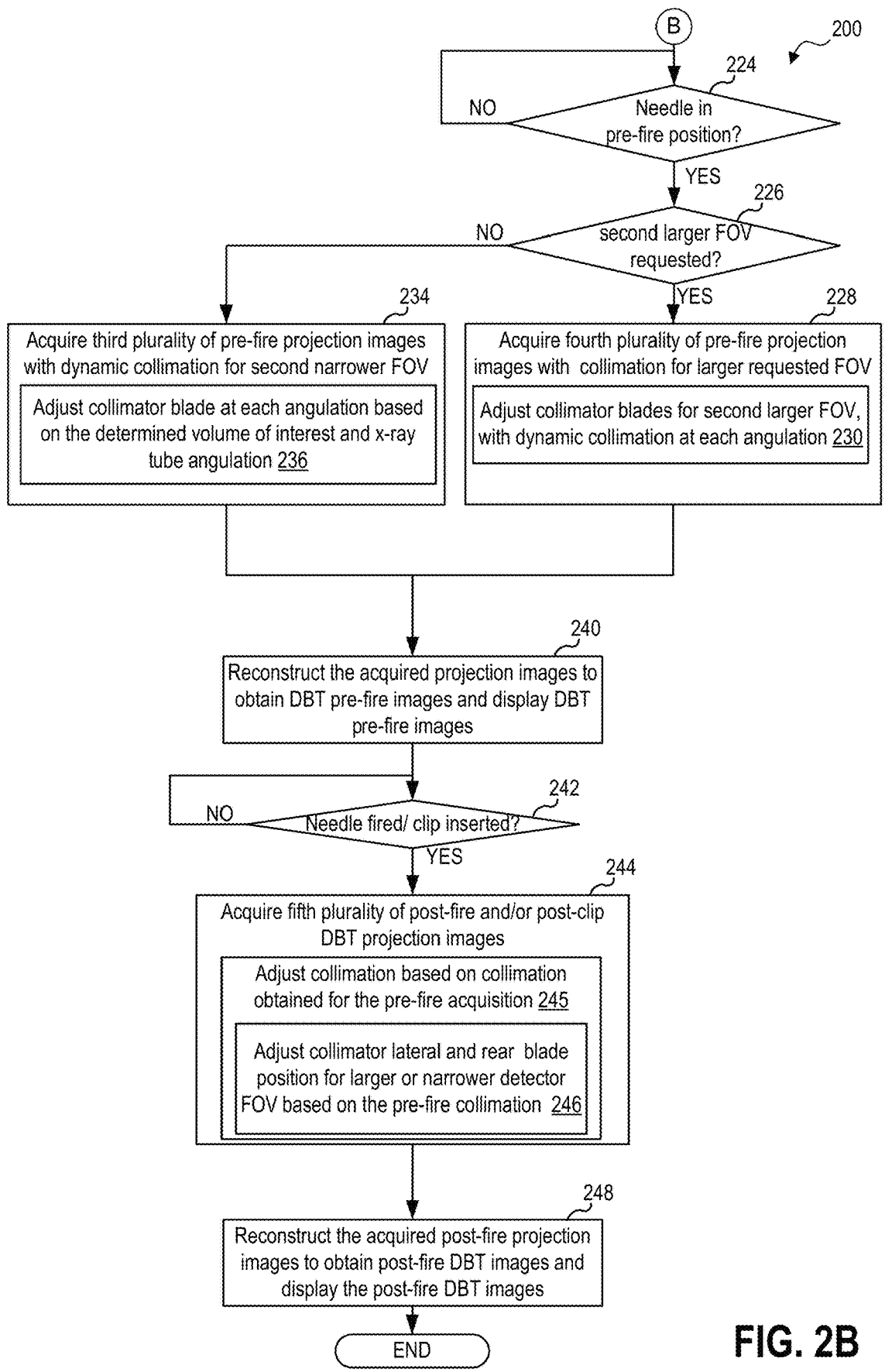
FIG. 2B is a continuation of FIG. 2A.

An exemplary method for dynamic collimation, wherein collimation is adjusted based on imaging requirements during a procedure performed with the x-ray mammography system is discussed at FIG. 2A and FIG. 2B. Specifically, dynamic collimation adjustment during DBT-guided biopsy is illustrated. As an example, prior to selecting a target for biopsy, collimation may be adjusted to provide a greater field of view to obtain views for positioning and target identification. In response to the user selecting the target, the collimation may be adjusted to limit irradiation to a volume of interest determined based on the target selection. Thus, an area to irradiate on the detector determined by the collimation is based on the volume of interest computed based on the target selection. Further, during DBT acquisition, the x-ray source is rotated within an angular range of the x-ray system to obtain plurality of images at plurality of angles within the angular range. The collimation may be further adjusted based on the rotation angle of the x-ray tube during DBT acquisition. As a result, at each angular position of the x-ray tube, the collimation is adjusted. Thus, the area to irradiate on the detector is changed at each angular position of the x-ray source. Additionally, the volume of interest is based on breast thickness and compression paddle parameters.

The collimation adjustment wherein the collimation is changed such that the area to irradiate on the detector is changed based on one or more of the volume of interest and angular position of the x-ray source is referred to as dynamic collimation. The dynamic collimation may be implemented during a single acquisition procedure, such as during a tomosynthesis acquisition, wherein at each angulation the collimation and the detector area to irradiate are changed to image the volume of interest. Further, the dynamic collimation may be implemented at different workflow steps during an imaging procedure (e.g. before and after target selection or region of interest selection) wherein collimation is changed to image different volume of interest depending on the workflow step. Furthermore, the dynamic collimation may be implemented in one or more of screening, diagnostic, and interventional procedures performed with the mammography system as discussed further below.

In some embodiments, during an image-guided interventional procedure, prior to selecting a target, a first tomosynthesis scan of a compressed breast may be performed with first collimation at a plurality of angular positions of an x-ray source of the x-ray system, and a first set of images may be reconstructed from first tomosynthesis scan data. Further, responsive to target selection from the first set of images, a second tomosynthesis scan of the compressed breast may be performed with second collimation at the plurality of angular positions of the x-ray system, and a second set of images may be reconstructed from first tomosynthesis scan data. The first collimation may be based on a greater volume of interest; and the second collimation is based on a reduced volume of interest. The first collimation may be further based on a corresponding x-ray source angulation. The first collimation is adjusted to irradiate a corresponding greater area on a detector of the x-ray system at each of the plurality of angular positions. The second collimation is further based on the corresponding x-ray source angulation. The second collimation is adjusted to irradiate a corresponding reduced area on the detector at each of the plurality of angular positions. Further, each of the greater area and the reduced area is changed at each angular position by adjusting one or more of lateral and rear collimator blade positions at each angular position. Furthermore, a first average detector area irradiated during the first tomosynthesis scan may be greater than a second average detector area irradiated during the second tomosynthesis scan.

Figure 2C:
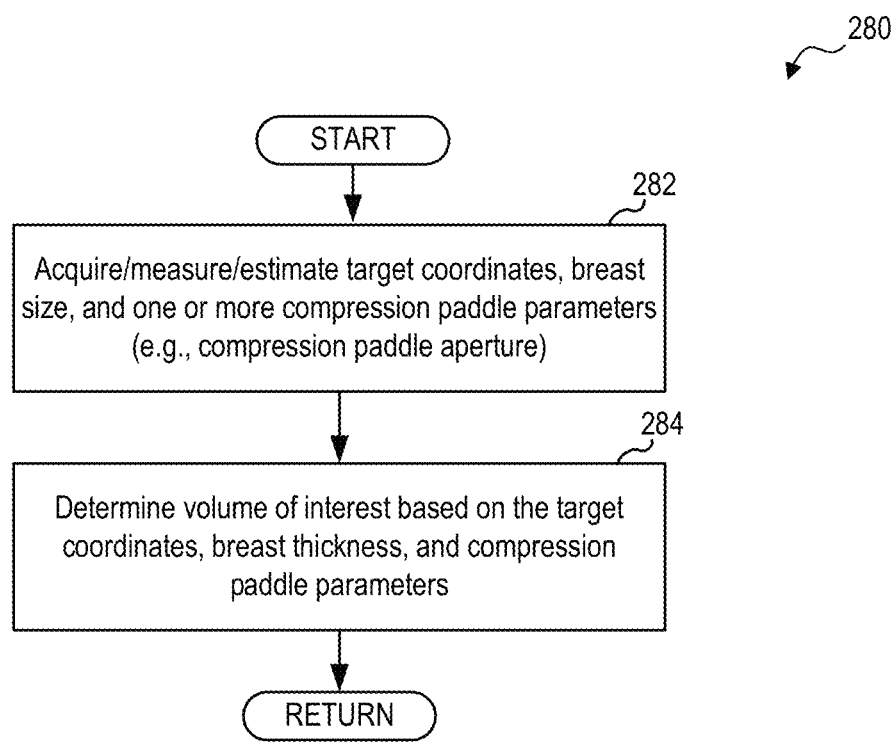
FIG. 2C a high-level flow chart illustrating a method for determining a volume of interest for adjusting collimation, according to an embodiment of the disclosure.
Figure 3C:
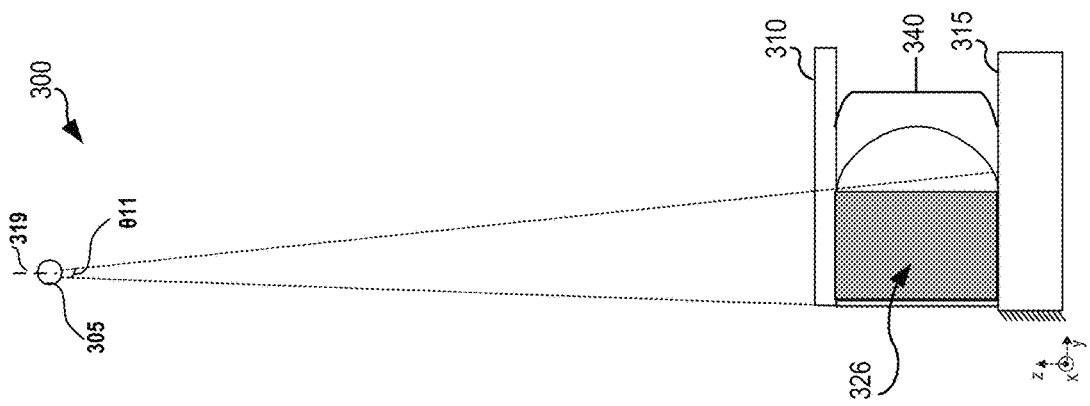
FIG. 3C is another schematic illustration of dynamic rear collimation, according to an embodiment of the disclosure.
Figure 3B:
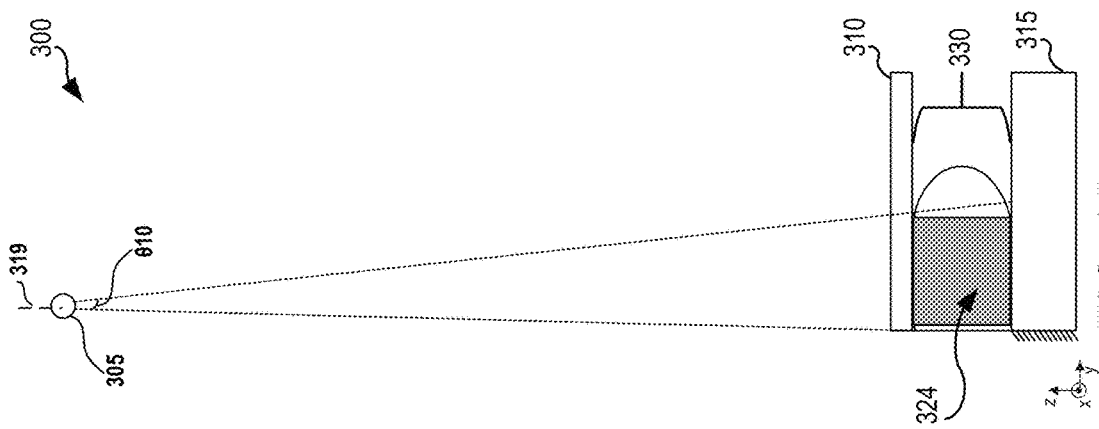
FIG. 3B is a schematic illustration of dynamic rear collimation, according to an embodiment of the disclosure.
Figure 3A:
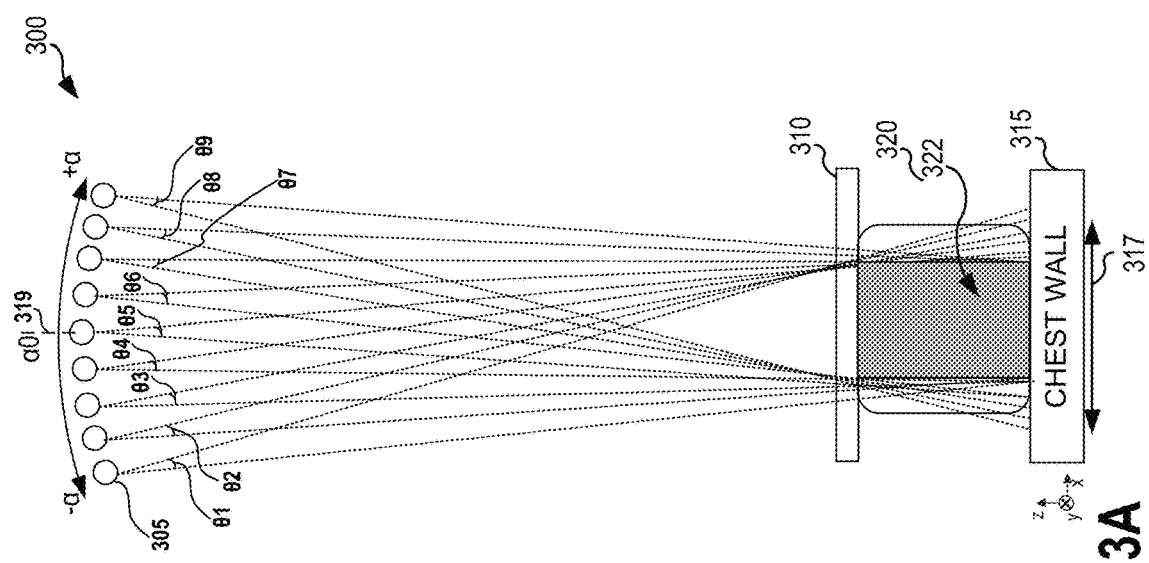
FIG. 3A is a schematic illustration of dynamic lateral collimation, according to an embodiment of the disclosure.
Figure 3D:
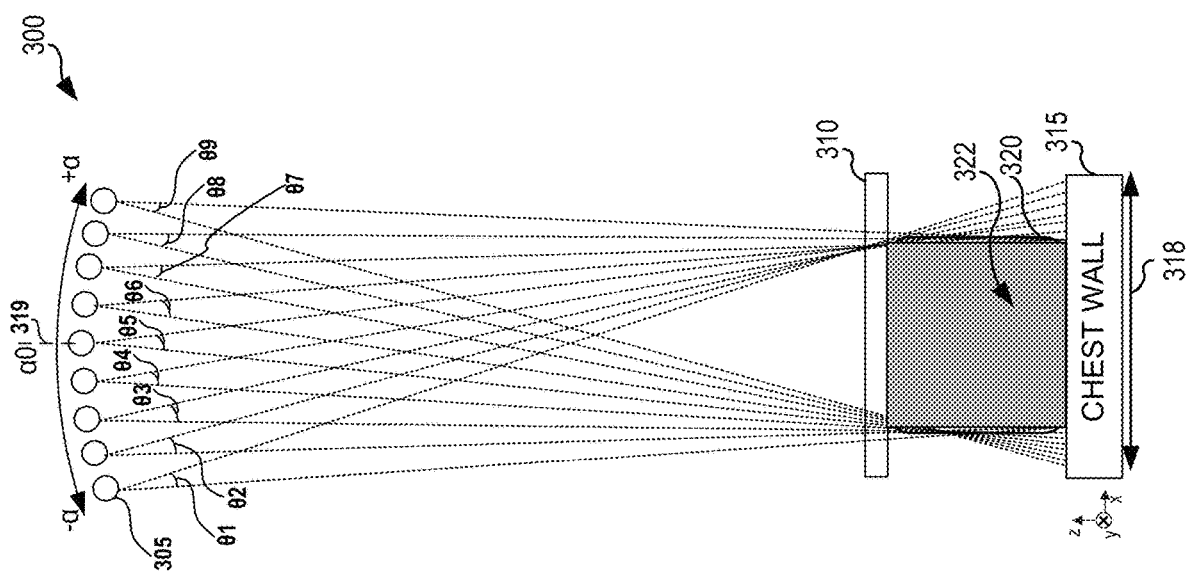
FIG. 3D shows a schematic illustration of exemplary collimation at different x-ray source angular positions prior to target selection, according to an embodiment of the disclosure.
Figure 4C:
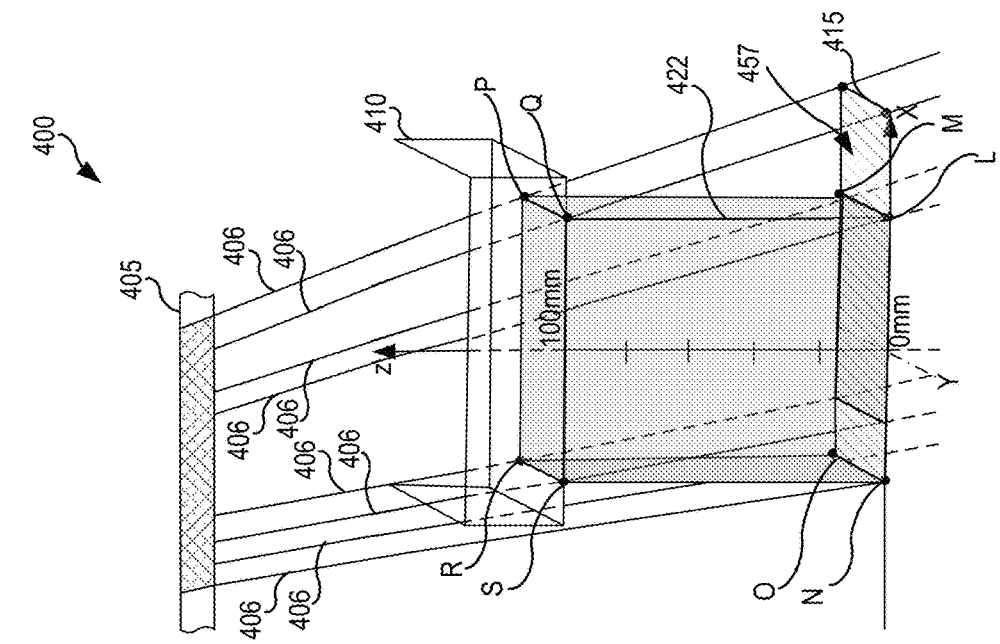
FIGS. 4A, 4B, and 4C show three-dimensional illustration of dynamic collimation, including respective areas of irradiation at three different x-ray source angular positions, according to an embodiment of the disclosure.
Figure 4B:
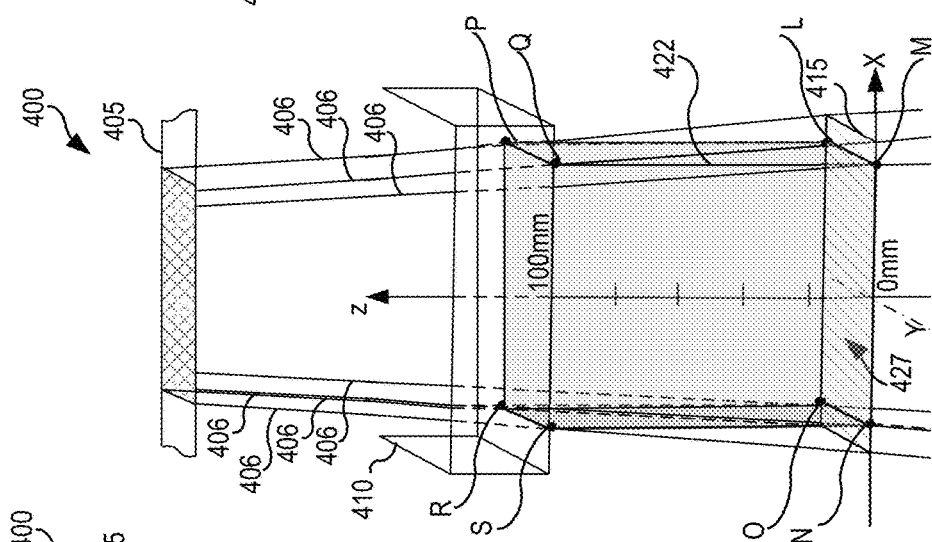
Figure 4A:
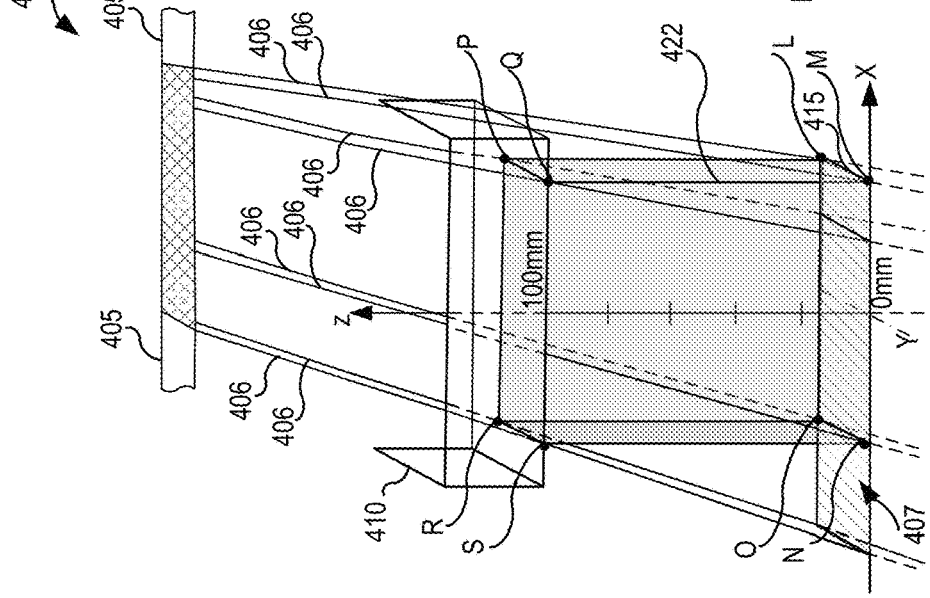
Figure 6:
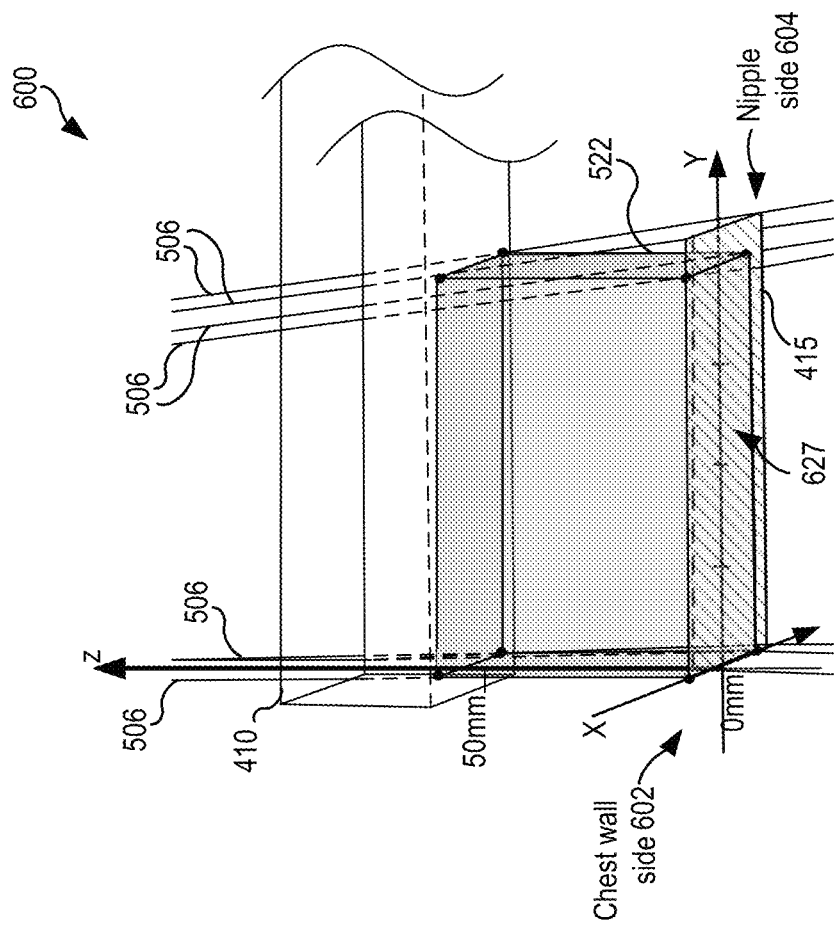
FIG. 6 shows three-dimensional illustration of dynamic rear collimation, according to an embodiment of the disclosure.

In this way, by adjusting collimation differently at different workflow steps (e.g., prior to target selection and after target selection) a total area to irradiate may be reduced. This in turn results in reduced radiation exposure to the patient while improving resolution of the volume of interest. An example high-level flow chart illustrating determination of volume of interest is shown at FIG. 2C. Exemplary schematic illustrations of dynamic collimation adjustment during DBT acquisitions after a biopsy target is selected is shown at FIGS. 3A-3C. Further, FIG. 3D shows an exemplary schematic illustration of collimation prior to target selection, wherein the collimation is adjusted so that the area irradiated on the detector is changed for each x-ray source angulation during the DBT acquisition to image a larger volume of interest. Three-dimensional illustrations of the volume of interest and area to irradiate at different angular positions of the x-ray tube during DBT acquisition after target selection is depicted at FIGS. 4A-4C. Further, as the breast thickness decreases the area to irradiate decreases for the same angular positions of the x-ray tube as illustrated at FIGS. 5A-5C. Furthermore, FIG. 6 shows an exemplary three-dimensional illustration of rear collimation adjustment and a side view of the area to irradiate. An exemplary method for dynamically changing the detector area to irradiate for stereo guided biopsy and CESM guided biopsy is discussed at FIG. 7. An exemplary illustration of lateral collimation adjustment for a CC view that may be utilized during stereo guided and/or CESM guided biopsy after biopsy target selection is shown in FIG. 8A. Rear collimation adjustment for different breast thickness is illustrated at FIGS. 8B and 8C. By dynamically changing the detector area to irradiate after target selection based on the volume of interest, and x-ray source angulation during image guided biopsy procedures with the x-ray mammography system, including DBT guided biopsy, stereo guided biopsy, CESM guided biopsy, Contrast enhanced DBT (CE-DBT) guided biopsy, imaging artifacts, due to accessories such as biopsy device, biopsy needle, etc., for example, may be reduced as the collimated x-ray beam is limited to the reduced volume of interest. An exemplary reduction in imaging artifact is illustrated with exemplary scan images at FIG. 9.

Referring to FIG. 1A, a mammography system 100 including an x-ray system 10 for performing a mammography procedure is shown, according to an exemplary embodiment. The x-ray system 10 may be a tomosynthesis system, such as a digital breast tomosynthesis ("DBT") system, and may be used to perform one or more procedures including digital tomosynthesis imaging, and DBT guided breast biopsy. Further the x-ray system 10 may be utilized to perform one or more of dual energy CESM, contrast enhanced DBT (CE-DBT) diagnostic, and interventional stereotactic procedures.

The x-ray system 10 includes a support structure 42, to which a radiation source 16, a radiation detector 18, and a collimator 20 are attached. The radiation source 16 is housed within a gantry 15 that is movably coupled to the support structure 42. In particular, the gantry 15 may be mounted to the support structure 42 such that the gantry 15 including the radiation source 16 can rotate around an axis 58 in relation to the radiation detector 18. An angular range of rotation of the gantry 15 housing the radiation source 16 indicates a rotation up to a desired degree on either directions from a vertical axis perpendicular to a horizontal detection surface of the detector 18 For example, the angular range of rotation of the radiation source 16 may be −a to +a, where a may be such that the angular range is a limited angle range, less than 360 degrees. An exemplary x-ray system may have an angular range of +15 degrees, which may allow rotation of the gantry (that is rotation of the radiation source) from −15 degrees to +15 degrees with respect to the vertical axis. The angular range may vary depending on the manufacturing specifications. For example, the angular range for DBT systems may be approximately +11 degrees to +60 degrees, depending on the manufacturing specifications.

The radiation source 16 is directed toward a volume or object to be imaged, and is configured to emit radiation rays at desired times and to acquire one or more images. The radiation detector 18 is configured to receive the radiation rays via a detection surface 24. The detector 18 may be any one of a variety of different detectors, such as an x-ray detector, digital radiography detector, or flat panel detector. The collimator 20 is disposed adjacent to the radiation source 16 and is configured to adjust an irradiated zone of object imaged.

In some exemplary embodiments, the system 10 may further include a patient shield 36 mounted to the radiation source 16 via face shield rails 38 such that a patient's body part (e.g., head) is not directly under the radiation. The system 10 may further include a compression paddle 40, which may be movable upward and downward in relation to the support structure along a vertical axis 60. Thus, the compression paddle 40 may be adjusted to be positioned closer to the radiation detector 18 by moving the compression paddle 40 downward toward the detector 18, and a distance between the detector 18 and the compression paddle 40 may be increased by moving the compression paddle upward along the vertical axis 60 away from the detector. The movement of the compression paddle 40 may be adjusted by a user via compression paddle actuator (not shown) included in the x-ray system 10. The compression paddle 40 may hold a body part, such as a breast, in place against the surface 24 of the radiation detector 18. The compression paddle 40 may compress the body part, and hold the body part still in place while optionally providing apertures to allow for insertion of a biopsy needle, such as a core needle, or a vacuum assisted core needle. In this way, compression paddle 40 may be utilized to compress the body part to reduce the thickness traversed by the x-rays and to help reduce movement of the body part due to the patient moving. The x-ray system 10 may also include an object support (not shown) on which the body part may be positioned.

The mammography system 100 may further include workstation 43 comprising a controller 44 including at least one processor and a memory. The controller 44 may be communicatively coupled to one or more components of the x-ray system 10 including one or more of the radiation source 16, radiation detector 18, the compression paddle 40, and a biopsy device. In one exemplary embodiment, the communication between the controller and the x-ray system 10 may be via a wireless communication system. In other exemplary embodiments, the controller 44 may be in electrical communication with the one or more components of the x-ray system via a cable 47. Further, in an exemplary embodiment, as shown in FIG. 1A, the controller 44 is integrated into workstation 43. In other exemplary embodiments, the controller 44 may be integrated into one or more of the various components of the system 10 disclosed above. Further, the controller 44 may include processing circuitry that executes stored program logic and may be any one of a different computers, processors, controllers, or combination thereof that are available for and compatible with the various types of equipment and devices used in the x-ray system 10.

The workstation 43 may include a radiation shield 48 that protects an operator of the system 10 from the radiation rays emitted by the radiation source 16. The workstation 43 may further include a display 50, a keyboard 52, mouse 54, and/or other appropriate user input devices that facilitate control of the system 10 via a user interface 56.

Through its processors and controllers, the controller 44 may adjust the operation and function of the x-ray system 10. As an example, the controller 44 may provide timing control, as to when the x-ray source 16 emits x-rays, and may further adjust how the detector 18 reads and conveys information or signals after the x-rays hit the detector 18, and how the x-ray source 16 and the detector 18 move relative to one another and relative to the body part. The controller 44 may provide collimation control, for example, by commanding a collimator actuator to adjust an amount of opening of the collimator via adjustment of one or more of lateral and rear blades of the collimator 20 so as to irradiate a volume of the object to be imaged, and thereby, control an area to irradiate on the detection surface 24. The controller 44 may also control how information, including images 42 and data acquired during the operation, is processed, displayed, stored, and manipulated. The different processing steps, including receiving one or more signals from one or more sensors, receiving user input, evaluating the received signals/input, image processing, determining imaging volume of interest (e.g., based on a user selected region of interest, based on user selected b target), commanding collimator adjustment during acquisitions and at various workflow steps, adjusting one or more actuators of the x-ray system to control operation of the x-ray system, performed by the controller 44, may be provided by a set of instructions stored in non-transitory memory of the processor. Information may also be stored in one or more non-transitory memories of controller 44 for later retrieval and use.

Further, as stated above, the radiation detector 18 receives the radiation rays emitted by the radiation source 16. In particular, during imaging with the x-ray system, a projection image of the imaging body part may be obtained at the detector 18. In some exemplary embodiments, data, such as projection image data, received by the radiation detector 18 may be electrically and/or wirelessly communicated to the controller 44 from the radiation detector 18. The controller 44 may then reconstruct one or more scan images based on the projection image data, by implementing a reconstruction algorithm, for example. The reconstructed image may be displayed to the user on the user interface 56 via a display screen 50.

The radiation source 16, along with the radiation detector 18, forms part of the x-ray system 10 which provides x-ray imagery for the purpose of one or more of screening for abnormalities, diagnosis, dynamic imaging, and image-guided biopsy. For example, the x-ray system 10 may be operated in a mammography mode for screening for abnormalities. During mammography, a patient's breast is positioned and compressed between the detector 18 and the compression paddle 40. Thus, a volume of the x-ray system 10 between the compression paddle 40 and the detector 18 is an imaging volume. The radiation source 16 then emits radiation rays on to the compressed breast, and a projection image of the breast is formed on the detector 18. The projection image may then be reconstructed by the controller 44, and displayed on the interface 50.

During mammography, the gantry 15 may be adjusted at different angles to obtain images at different orientations, such as a craniocaudal (CC) image and a mediolateral oblique (MLO) image. For example, when imaging CC and MLO views, the gantry 15, the compression paddle 40, and the detector 18 may be rotated as a single unit about the axis 58. In other examples, the gantry 15 may be rotated about the axis 58 while the compression paddle 40 and the detector 18 remain stationary.

Further, the x-ray system 10 may be operated in a tomosynthesis mode for performing digital breast tomosynthesis (DBT). During tomosynthesis, the x-ray system 10 may be operated to direct low-dose radiation towards the imaging volume (between the compression paddle 40 and the detector 18) at various angles over the angular range of the x-ray system 10. Specifically, during tomosynthesis, similar to mammography, the breast is compressed between the compression paddle 40 and the detector 18. The radiation source 16 is then rotated from −a degrees to +a degrees, and a plurality of projection images of the compressed breast are obtained at regular angular intervals over the angular range. For example, if the angular range of the x-ray system is +15 degrees, 31 projection images may be captured by the detector during an angular sweep of the gantry at approximately one every one degree. The plurality of projection images are then processed by the controller 44 to generate a plurality of DBT image slices. The processing may include applying one or more reconstruction algorithms to reconstruct three dimensional image of the breast.

Furthermore, the x-ray system may be configured to perform a DBT-guided biopsy procedure. Accordingly, in some exemplary embodiments, the system 10 may further include a biopsy device comprising a biopsy needle for extracting a tissue sample for further analysis. An exemplary biopsy device is illustrated at FIG. 1B.

Turning to FIG. 1B, a schematic illustration of a biopsy device 140 that may be used in conjunction with a mammography system, such as the mammography system 100 of FIG. 1A, is shown. The biopsy device 140 will be described herein with reference to the mammography system 100 at FIG. 1A. Biopsy device 140 includes a biopsy table 155 that is positioned over the detector 18 of the x-ray system 10. In one example, the biopsy table 155 may be configured to slide over the detector 18. During set-up of the biopsy device 140, the user may remove the compression paddle 40 of the x-ray system 10, and slide the biopsy table 155 over the detector 18. Upon positioning the biopsy device 140 on the x-ray system 10, a suitable compression paddle for biopsy (not shown), such as a horizontal approach biopsy paddle (without aperture) or vertical approach biopsy paddle (with aperture), depending on the type of biopsy, may be selected and coupled to the x-ray system 10.

A biopsy tool interface 160 having a biopsy tool display 162 may be coupled to the biopsy table 155 via a communication port 164. In one embodiment, the biopsy tool interface 160 may be communicatively coupled with the x-ray system controller 44, as indicated by double ended arrow 154, and as such, the user may be able to adjust a position of the x-ray system via the biopsy tool interface 160. In other embodiments, the biopsy tool interface 160 may be coupled to a biopsy device controller 150, which sends and receives information to and from the x-ray system controller 44 (as indicated by double ended arrow 152). In some other embodiments, additionally or alternatively, adjustment and control of the biopsy device 140 may be performed by a biopsy device control module 159 of the x-ray system controller 44.

Biopsy device 140 includes a biopsy tool 170 that may be directly coupled to the biopsy table 155. The biopsy tool 170 includes a robotic system comprising a trunk 172 to which a first arm 174 is attached. The biopsy tool 170 may further include a second arm 176 that is coupled to the first arm 174 on one end and coupled to a biopsy gun holder 180 at a second opposite end. The second arm 176 may be pivoted with respect to the first arm 174 to adjust a position of the biopsy gun holder. The illustration in FIG. 1B shows the biopsy tool 170 configured in a vertical approach for biopsy. The vertical approach involves inserting the needle into the breast in a direction perpendicular to a horizontal plane of the compression paddle. Thus, during setting up the biopsy device in the vertical approach, the biopsy gun holder 180 is positioned such that a longitudinal axis of the biopsy gun holder 180 along a length of the biopsy gun holder 180 is parallel to z-axis 141 and perpendicular to a horizontal surface 156 of the biopsy table 155.

The biopsy tool 170 may be adjusted to perform biopsy in a horizontal approach where the needle is inserted into the breast in a direction parallel to the compression paddle. During setting up the biopsy device in the lateral approach, the second arm 176 may be pivoted by 90 degrees, via a knob 177, such that the longitudinal axis of the biopsy gun holder is perpendicular to z-axis 141 and parallel to the horizontal surface of the biopsy table 155.

The biopsy gun holder 180 may be utilized for mounting a biopsy gun 184. Further, the biopsy gun holder 180 may include a mechanical stop for adjusting a position of a biopsy needle 190. Specifically, during biopsy, prior to inserting the needle, the breast is positioned between a compression paddle (not shown) and surface 156. In some examples, a breast spacer may be positioned on the surface, and the breast is positioned between the compression paddle and the spacer, and compressed by moving the compression paddle toward the surface 156. Upon positioning the breast, a first set of targeting images are obtained by the scanning the compressed breast with x-ray system 10 at various angles over its angular range to identify a target for biopsy. The first set of targeting images may be three dimensional images (DBT images) or two-dimensional full field digital mammography images reconstructed from the x-ray system acquisitions. The user may localize the concerned region and identify a target position for biopsy by selecting the target position from the first set of images. The target position may be identified by x, y, and z coordinates within a DBT volume between the compression paddle and the biopsy table surface 156 or spacer (if used).

Upon selecting the biopsy target position, a second set of DBT images may be obtained, for example, post anesthesia and prior to inserting the needle. In this way, DBT images may be acquired at different workflow steps during DBT guided biopsy. Further, collimation may be adjusted at each workflow step so as to provide a first collimation, based on a first larger volume of interest, for acquisitions before target selection and a second collimation, based on a second smaller volume of interest, for acquisitions after target selection. Details of adjusting collimation during image acquisition at different workflow steps are further discussed below with respect to FIGS. 2A-2C, 3A-3D, 4A-4C, 5A-5C, 6, 7, and 8A-8C. Briefly, during any imaging procedure and/or image guided interventional procedure (e.g., biopsy), prior to target selection, the collimator 20 may be commanded to provide the first collimation, wherein the collimated x-ray beam output from the collimator 20 irradiates a larger volume of the compressed breast to identify the target tissue portion and position of the target tissue. For example, during a DBT acquisition, an area to irradiate on the detection surface after passing through the larger volume of the compressed breast may be adjusted at each x-ray tube angulation to include the larger volume prior to target selection. In particular, even if an x-ray source field of view is large to help positioning the breast, the area to irradiate on the detector is not maintained at each angulation, but adjusted in order to include the larger volume of interest at each angulation.

After target selection, the collimator 20 may be commanded to provide the second collimation, wherein at each angulation of the x-ray source, the collimator 20 is adjusted to limit irradiation to a reduced volume of interest, the reduced volume including the target (and hence, including a regional volume of the breast comprising the target). In some examples, a margin volume may be added to the reduced volume of interest in order to image a slightly larger portion of the breast. It will be appreciated that the total volume of breast irradiated (that is, including reduced volume and margin volume) after target selection is less than the larger volume irradiated prior to target selection.

Further, the collimator 20 is adjusted based on the x-ray tube angulation such that at each angulation the collimated x-ray beam is limited to irradiate the reduced volume of interest. The collimator adjustment after target selection may be based on a corresponding area to irradiate on the detector at each angulation. In this way, the area irradiated on the detector is adjusted dynamically to image the reduced volume of the breast post target selection. This reduces radiation exposure to the patient in one or more post target selection steps as the imaged area is reduced to the reduced volume of interest. Further, by limiting the imaged portion to the reduced volume of interest, imaging artifacts due to the images capturing metallic objects (e.g., from portions of biopsy device) are reduced. Furthermore, the time to reconstruct images post target selection is reduced. Further still, during CESM guided biopsy procedures, the imaging artifacts are dependent on a scatter amount. By reducing the irradiated area, the scatter amount may be reduced.

Further, based on the target position coordinates selected by the user, the biopsy device controller 150 may adjust the mechanical stop position of the biopsy gun holder 180 such that when the needle is inserted into the compressed breast via the biopsy gun 184, the needle movement is stopped when the needle tip reaches a desired position with respect to the target position. While the present example illustrates adjustment of the biopsy device via the biopsy device controller 150, it will be appreciated that in some embodiments, the x-ray system controller 44 may command control of the biopsy device 140. In this way, during biopsy in the vertical approach mode, the depth position of the biopsy needle may be adjusted with the biopsy gun 184 and biopsy gun holder 180.

Further, the biopsy tool 170 may include a platform 173 and a rail 177. The trunk 172 of the biopsy tool 170 may move over the platform 173 parallel to x-axis 143. Movement of the biopsy tool 170 over the platform 173 is indicated by double ended arrow 147. The movement of the trunk along the platform 173 may be adjusted by the controller 150. Thus, during biopsy, the position of the biopsy gun and gun holder may be adjusted along the direction of x-axis such that an x-axis coordinate of the needle position is adjusted with respect to the target position. Further, the platform 173 may move in a direction of y-axis 142 along the rail 177. Movement of the biopsy tool 170 in the direction of y-axis is indicated by double ended arrow 148. Thus, during biopsy, the position of the biopsy gun and gun holder may be adjusted along the direction of y-axis such that a y-axis coordinate of the needle position is adjusted with respect to the target position. Furthermore, the biopsy tool 170 may move upward and downward, as indicated by double ended arrow 149. For example, the arm 174 may be movable in the direction of z-axis 141 indicated by arrow 149 to adjust a position of the biopsy gun holder 180 (and thus, the biopsy gun 184 and the biopsy needle 190) along the z-axis 141. The movement of the biopsy tool, in the x, y, and z directions may be adjusted by the controller 150. It will be appreciated that embodiments where the adjustment of the biopsy tool in one or more of the x, y, z, directions is performed manually in addition to or alternative to the adjustment by the controller are also within the scope of the disclosure.

Taken together, during biopsy, upon selection of target position from the first set of targeting images obtained by the x-ray system, prior to inserting the needle 190, the controller (which may be x-ray system controller 44 or biopsy device controller 150), may adjust position of the biopsy needle by adjusting the biopsy tool in the direction 147 of x axis, in the direction 148 of y axis, in the direction 149 of z-axis and adjusting the mechanical stop position based on the target position coordinates such that when the needle is inserted the needle tip is at the desired position in the breast tissue with respect to the target position.

In this way, the robotic system of the biopsy tool 170 may be utilized to adjust the needle position and biopsy tool position based on the target position computed from images. Once the biopsy tool and the biopsy gun are at target position, the user/radiologist may drive the needle through the biopsy gun 184 until it reaches the mechanical stop. Once fully inserted, the needle is then at the target position (that is, the position where a notch of the needle is in a position within the tissue with respect to the lesion to puncture, but has not yet excised the lesion).

Once the needle is inserted, the needle is at a pre-fire position. During DBT guided biopsy, when the needle is at the pre-fire position, a plurality of pre-fire images may be obtained. In one embodiment, the collimator 20 may be adjusted dynamically at each angulation of the x-ray source to irradiate the reduced volume of interest during acquisition of the plurality of pre-fire images. The pre-fire images may be utilized to confirm the position of the biopsy needle (specifically, a needle tip) with respect to the biopsy target. As the reduced volume of interest is imaged, pre-fire images may be reconstructed at a faster rate. Further, images of metallic objects in the vicinity of the reduced volume are reduced.

Upon confirmation of the biopsy needle position based on the pre-fire images, the biopsy gun 184 may be deployed to fire the biopsy needle. After needle firing (post-fire), a plurality of post-fire images may be obtained to evaluate the position of a notch of the needle with respect to the target, for example. Subsequently, the targeted tissue may be extracted. After extraction, a post-biopsy clip may be inserted at or near the biopsy site to mark the location of biopsy. After extraction and insertion of the biopsy clip, a plurality of post-clip images may be obtained. In one embodiment, the collimator 20 may be adjusted to irradiate the reduced volume of interest during the post-fire images and/or the post-clip images. As the reduced volume of interest is imaged, post-fire images and/or post-clip images may be reconstructed at a faster rate. As a result, the entire biopsy procedure may be performed at a faster rate, leading to improved patient care and comfort.

While collimation adjustment is described herein with respect to a biopsy procedure, it will be appreciated that the collimation adjustment, wherein the collimator is adjusted to adjust an area irradiated on the detector based on a corresponding volume of interest at different workflow steps so as to limit irradiation the corresponding volume, may be implemented for any other interventional or diagnostic procedure performed with the x-ray system. An example interventional procedure may include a breast chirurgic procedure, wherein a hook wire is deployed and the target is a clip. While evaluating a hook wire position within the breast (e.g., after hook wire deployment), collimation may be adjusted based on a target volume having a target region of interest. Another example procedure may be an image guided cryoablation procedure.

Details of the collimation adjustment are described with respect to FIGS. 2A-2C, 3A-3D, 4A-4C, 5A-5C, 6, 7, and 8A-8C below.

Turning to FIG. 2A, it shows a high-level flow chart illustrating a method 200 for adjusting collimation during a DBT-guided biopsy procedure with an x-ray imaging system, such as x-ray system 10 at FIG. 1A, and a biopsy device, such as biopsy device 140 at FIG. 1B. The method 200 may be implemented by an image processing system, such as controller 44 at FIG. 1A, an edge device connected to the image processing system, a cloud in communication with the image processing system, or any appropriate combination thereof. The method 200 is described with regard to the systems and components of FIG. 1A and FIG. 1B, although it should be appreciated that the method 200 may be implemented with other systems and components without departing from the scope of the present disclosure.

The method 200 begins at 202. At 202, the method 200 includes confirming if the x-ray system is operated in a DBT-guided biopsy mode. In one example, the mode of operation of the x-ray system may be determined based on an indication from a user on a user interface of the x-ray system. For example, the controller may determine the mode of operation based on the user launching an application interface corresponding to the mode of operation (e.g., launching a DBT-guided biopsy interface). Thus, in response to the user launching the DBT-guided biopsy interface, the DBT-guided biopsy mode may be confirmed. In another example, the mode of operation may be determined based on a vision sensing system detecting the presence of one or more accessories associated with the DBT guided biopsy procedure such as the biopsy device positioned on a detector surface of the x-ray system. In this case, the application interface for DBT-guided biopsy may be automatically launched, and the controller may determine that the x-ray system is used for DBT-guided biopsy based on one or more of an indication from the vision sensing system and the launch of the DBT-guided biopsy interface.

If DBT-guided biopsy mode is not confirmed, the answer at 202 is NO, and the method 200 proceeds to 203. At 203, the method 200 includes operating the x-ray system based on a user indicated mode. For example, the user indicated mode may be a mammography mode that may include a 2D screening mode, 2D diagnostic mode, DBT screening mode, DBT diagnostic mode, CESM diagnostic mode, stereo guided biopsy mode, and CESM guided biopsy mode, and a quality check mode. An exemplary method for adjusting collimation of the x-ray system during the CESM guided biopsy or the stereo guided biopsy mode is further described below with respect to FIG. 8.

If DBT-guided biopsy mode is confirmed, the answer at 202 is YES, and the method 200 proceeds to 204. At 204, the method 200 includes confirming if the breast is positioned for biopsy. This includes determining if the breast is compressed between the compression paddle and the detector surface, and may include determining if a spacer is utilized to support the breast during compression. In one example, the confirmation of breast positioning may be based on an indication from the user via the user interface of the x-ray system to initiate a first image acquisition. For example, upon positioning the breast for biopsy, the user may initiate the first image acquisition to obtain one or more positioning views of the breast that may be utilized to identify a target for biopsy. In another example, the confirmation of breast positioning may be based on an indication from the user via the user interface that the breast positioning is complete.

If the breast position is not confirmed for biopsy (e.g., when the user is in the process of adjusting the patient for biopsy, prior to positioning the patient, etc.), the answer at 204 is NO, and the controller continues to monitor the x-ray system for positioning confirmation.

If the breast position is confirmed for biopsy, the answer at 204 is YES, and the method 200 proceeds to 206.

At 206, the method 200 includes acquiring a first set of projection images with collimation adjusted to irradiate a greater volume of the breast. Specifically, the collimator is adjusted such that a detector field of view is at a first greater field of view covering the greater volume of the breast (e.g., entire breast). Said another way, the collimator blades are adjusted such that the x-ray beam is collimated to irradiate the greater volume of the breast, and as such, a detector area irradiated by the collimated x-ray beam after passing through the breast tissue is greater for the greater volume of breast. This results in a first greater detector field of view. The detector area is also referred to herein as projection field of view. The collimation obtained when the collimator is adjusted to irradiate the greater volume of the breast as discussed above may be referred to as the first collimation. Adjusting the collimator blades may include adjusting the lateral blades as well as the rear blades. It may be noted that the first image acquisition with the first collimation is obtained prior to selecting the target for biopsy, and is utilized to identify the target and specify the target coordinates for biopsy.

Acquiring the first set of projection images with the first collimation includes, at 207, obtaining one or more 2D positioning projection images, and a plurality of DBT targeting projection images. For example, the one or more 2D positioning views may be obtained with the x-ray tube at a medial position at which a vertical axis, such as vertical axis 60 at FIG. 1A, of the x-ray tube is perpendicular to the top detection surface of the detector. The collimator may be adjusted to irradiate the larger volume of breast.

Further, the plurality of DBT targeting projection images may be obtained with the collimator adjusted to irradiate the greater portion of breast. During acquiring the plurality of DBT targeting images, the x-ray tube may be rotated within the angular range of the x-ray tube, and a plurality of images may be acquired at each of a plurality of angles within the angular range. In one example, at each angulation of the x-ray tube, prior to selecting the target for biopsy, the collimator may be adjusted so that the area irradiated on the detector is changed at each angulation of the x-ray tube to image the large volume of interest. In this way for positioning and target identification, a volume of the breast imaged is larger for ease of target identification and patient positioning. Further, by adjusting collimation (that is, by implementing dynamic collimation) to include the entire larger volume of interest at each angulation, imaging resolution in improved. An example illustration of the first collimation and detector area irradiated prior to target selection is shown at FIG. 3D.

Next, at 208, the method 200 includes reconstructing a first set of images from the projection images, and displaying the first set of images. The first of images are reconstructed from the one or more 2D positioning projection images, and the plurality of DBT targeting projection images. Thus, the first set of images includes one or more 2D images of the breast (reconstructed from the one or more 2D positioning projection images) and a three dimensional image of the breast including a plurality of DBT image slices (reconstructed from the plurality of DBT targeting projection images). The first set of images may be displayed on the user interface. The user may utilize the first set of images to identify the target for biopsy. For example, the user may view the one or more 2D positioning images. Further, the user may view the plurality of DBT image slices one by one to identify the target plane, and identify the target. The target may be identified by the user selecting the target on an image slice of the plurality of DBT image slices.

Continuing on to 210, the method 200 includes determining if the target is received at the controller. For example, the controller may determine if a target location for biopsy is identified based on user selection of the target on one or more of the 2D positioning images and the plurality of DBT image slices. The target location for biopsy may be within a region of interest and may be selected by the user, via the x-ray system user interface and/or the biopsy tool interface, based on identification of an abnormality from the first set of reconstructed images. The abnormality may be an indication of breast cancer and may include one or more of lesion, microcalcification, architectural distortion, and any deviation from normal breast anatomy that may be an indication of breast cancer. The user may select the target by highlighting the target location, for example. The target location may be alternatively referred to herein as the target position or simply as the target.

If the target is not identified, the answer at 210 is NO, and the method 200 proceeds to 211. At 211, the controller may prompt user to identify the target, and the method may return to 210 to determine if the target has been selected.

If the target is identified by the user/received at the controller, the answer at 210 is YES, and the method 200 proceeds to 212.

At 212, the method 200 includes determining, for each angulation of the x-ray source, a corresponding detector area to irradiate based on a reduced volume of interest and the corresponding x-ray source angulation. The reduced volume of interest encompasses the target, and thus is determined based on the selected target biopsy coordinates, breast size (e.g., thickness), and one or more compression paddle parameters (e.g., compression paddle aperture size and location). Further, in one example, the reduced volume of interest may include a margin volume surrounding a biopsy volume including the biopsy target. In this example, the margin volume is considered to calculate the detector area to irradiate. Further details of determining the reduced volume of interest is discussed below at FIG. 2C.

Turning to FIG. 2C, a high-level flow chart illustrating a method 280 for determining the reduced volume of interest after target selection during an image guided interventional procedure, such as a DBT guided biopsy procedure, performed with an x-ray mammography system, such as the x-ray system 10 at FIG. 1A, is shown. Method 280 may be implemented by an image processing system, such as controller 44 at FIG. 1A, an edge device connected to the image processing system, a cloud in communication with the image processing system, or any appropriate combination thereof.

Method 280 begins at 282. At 282, the method 280 includes acquiring/measuring/estimating target coordinates, breast size, and one or more compression paddle parameters. The target coordinates may be determined as discussed above, based on user selection of the target. While the above example describes the target for a biopsy procedure, it will be appreciated that the target may be a region of interest selected by the user for better visualization of the selected region of interest, such as during a screening or diagnostic imaging procedure for example. In this case, the volume of interest may be based on coordinates of the selected region of interest, breast size, and the x-ray tube angulation at which the imaging volume is irradiated.

The breast size may include a breast thickness. The breast thickness may be the compressed breast thickness, and in one example, may be based on user indication. In another example, the compressed breast thickness may be based on a position of the compression paddle. For example, a position sensor coupled to the compression paddle may be used to determine at which position on the z-axis the compression paddle is stopped. In yet another example, the compressed breast thickness may be based on input from a vision sensor. In still another example, the breast size, including breast thickness, may be obtained from a sensor-based compression paddle that measures breast size (e.g., to determine a desired compression pressure).

Further, the one or more compression paddle parameters may include a compression paddle aperture. For example, during a vertical biopsy approach, the user may have access to the breast through one or more paddle apertures, and as such the reduced volume of interest may be based on the one or more compression paddle aperture size and location with respect to the target.

Next, the method 280 proceeds to 284. At 284, the method 280 includes determining the reduced volume of interest based on the target coordinates, the breast thickness, and the one or more compression paddle parameters. In one embodiment, the reduced volume of interest may be calculated as a function of biopsy volume (based on a target location, a size of biopsy target, and a biopsy needle selected), the compressed breast thickness, and paddle aperture parameters (e.g., size and location) of a selected paddle. In another embodiment, the reduced volume of interest may be calculated based on radiologist selection of the reduced volume, via the user interface for example. In still further embodiments, the volume of interest may be selected to image only the useful breast volume, and as such, other patient body parts, such as the contralateral breast, belly, etc., may be excluded from the selected volume of interest.

Upon determining the reduced volume of interest, the method 280 returns to step 212 at FIG. 2A to determine the corresponding area to irradiate on the detector.

For a given reduced volume of interest, the detector area to irradiate depends on the x-ray tube angulation. For example, once the target is identified and received by the controller, the reduced volume of interest is determined as discussed above based on the target coordinates, the breast thickness, and the compression paddle aperture parameters; and the detector area to irradiate after target selection is determined based on the reduced volume of interest and the x-ray tube angulation. Thus, for each x-ray tube angulation, the detector area to irradiate is different. Specifically, the detector area to irradiate is changed at each angulation to include the entire reduced volume of interest while excluding the surrounding breast volume outside the reduced volume of interest. In this way, at each x-ray tube angulation, corresponding irradiated detection area (alternatively referred to herein as detector area to irradiate, or area to irradiate) is focused to image the volume of interest that includes the biopsy target. By determining the detector area to irradiate based on the reduced volume of interest and x-ray source angulation, a total volume of breast imaged after target selection is reduced. As a result, an amount of radiation received by the patient is reduced, and further, time taken to reconstruct the DBT projection images is reduced, while achieving improved spatial resolution.

In order to achieve the dynamic detector irradiation, the collimation is adjusted at each angle, as discussed below. The change in detector area based on the volume of interest and the x-ray tube angulation after target selection for DBT guided biopsy is further illustrated and described with respect to FIGS. 3A-3C, 4A-4C, 5A-5C, 6, and 7.

Upon determining the detector area to irradiate for each x-ray tube angulation after target selection, the method 200 proceeds to 214. At 214, the method 200 includes acquiring a second plurality of projection images. The second plurality of projection images are DBT projection images obtained by imaging the reduced volume of the compressed breast at plurality of angles within the angular range of the x-ray system. The second plurality of DBT projection images are obtained with dynamic detector collimation such that at each angulation of the x-ray source, the area irradiated on the detector is changed to image the reduced volume of interest, and exclude surrounding volume. Thus, acquiring second plurality of projection images includes, at 216, adjusting collimation at each angulation to obtain a second narrower detector field of view, the second narrower field of view based on the area to irradiate calculated at each angulation.

The collimation is achieved by adjusting the collimator blades at each x-ray tube angulation. Said another way, the collimator blades are adjusted at each x-ray tube angulation based on the determined area (at 212) to irradiate at each angulation. Thus, adjusting collimation for a second narrower field of view at each angulation includes, at 217, adjusting one or more lateral and rear collimator blades to focus irradiation on the volume of interest such that for each angle, the corresponding determined area to irradiate on the detector is irradiated (by the collimated x-rays) and corresponding projection images are obtained at the detector.

As an example, at a first angulation $-\alpha 1$ of the x-ray source, a first detector area to irradiate A1 may be determined based on the reduced volume of interest and the first angulation $-\alpha 1$. The collimator lateral and rear blades may be adjusted to provide a first dynamic collimation such that a first collimated x-ray beam passes through the reduced volume of interest and irradiates the area A1. A first projection image of the reduced volume of interest of the breast is thus obtained at the detector with the first dynamic collimation at the first angulation $-\alpha 1$. The x-ray source is then rotated to a second angulation $-\alpha 2$ at which the collimator lateral and rear blades are again adjusted to provide a second dynamic collimation such that a second collimated beam irradiates area A2 determined based on the reduced volume of interest and the second angulation $-\alpha 2$. A second projection image includes projection of the reduced volume of interest of the breast obtained with the second dynamic collimation at the second angulation $-\alpha 2$. Similarly, if the x-ray tube is rotatable at N angles within the angular range of the x-ray system, A1, A2 . . . An areas are determined, and corresponding projection images are obtained.

In this way, at plurality of angulations of the x-ray source, a plurality of detector areas to irradiate are determined, and the collimator is adjusted at each of the plurality of angulations based on the corresponding detector area to irradiate, and the plurality of projection images for the reduced volume of interest of the breast are obtained.

Next, at 220, the method 200 includes reconstructing the second plurality of projection images to obtain a second three dimensional breast image of the reduced volume of interest, the second breast image including a second plurality of DBT image slices.

The second plurality of projection images as discussed above may be obtained post-anesthesia (after anesthesia is administered to the patient) after the user selects the biopsy target, and before inserting the biopsy needle into the breast to a pre-fire position. The user may utilize the second plurality of images to confirm the target region having the biopsy target.

In one embodiment, prior to target selection, the x-ray system may automatically apply dynamic collimation for the greater field of view, wherein collimation at each x-ray tube angulation is adjusted to irradiate the larger volume of interest and thus, image the larger volume. After target selection, the x-ray system may automatically switch to dynamic collimation for a narrower detector field of view and obtain projection images for the reduced volume.

Continuing on to FIG. 2B, method 200 includes, at 224, confirming if the biopsy needle is in the pre-fire position within the breast. In particular, the position where a notch of the needle is in a position within the tissue before reaching the lesion (that is, target tissue) to excise may be referred to as the pre-fire position. The pre-fire position may be determined based on an input from the user indicating via the user interface that the needle is in the pre-fire position. Additionally or alternatively, the needle pre-fire position may be determined based on input from a biopsy tool control system, such as the biopsy device controller 150 at FIG. 1B. If the needle is not in pre-fire positon, the answer at 224 is NO, and the method 200 may continue to monitor if the biopsy needle is at the pre-fire position.

If the needle is at the pre-fire position, the answer at 224 is YES, and the method 200 proceeds to 226. At 226, the method 200 includes confirming if a second larger field of view is requested. For example, the user may desire to utilize a second larger field of view for subsequent DBT acquisitions, and as such may indicate, via the user interface, that a second larger field of view is desired. It will be appreciated that the user may choose to adjust the detector field of view via a biopsy interface at any step during the DBT-guided biopsy procedure.

If the second larger field of view is requested, the answer at 226 is YES, and the method 200 proceeds to 228. At 228, the method 200 includes acquiring a fourth plurality of pre-fire projection images with collimation adjusted for the requested second larger field of view. In one example, dynamic collimation may be provided for the second larger requested field of view. For example, based on the second larger requested field of view, a second larger volume of interest may be computed. The second larger volume of interest may include the biopsy target volume. Further, at each angulation, a corresponding larger detector area to irradiate may be calculated based on the second larger volume of interest. Furthermore, based on the larger area to irradiate calculated for each x-ray source angulation, the collimator may be adjusted to collimate the x-ray beam to irradiate the second larger volume of interest, and subsequently irradiate the larger area on the detector. In this way, based on the second larger detector field of view requested by the user, the fourth plurality of pre-fire projection images covering a second larger breast volume may be obtained with dynamic detector collimation. Accordingly, in one example, acquiring the fourth plurality of pre-fire projection images for larger requested field of view may include, at 230, adjusting one or more of rear and lateral collimator blade positions for second larger FOV, with dynamic collimation implemented (based on corresponding area to irradiate that is different for each angulation) at each x-ray tube angulation.

Returning to 226, if the second larger field of view is not requested, the answer at 226 is NO, and the method 200 proceeds to 234. At 234, the method 200 includes acquiring a third plurality of pre-fire projection images with dynamic detector collimation. This includes maintaining the second narrower detector field of view adjusted for each angulation as discussed above at step 214. Briefly, a corresponding detector area to irradiate at each x-ray source angulation is calculated based on the reduced volume of interest and the corresponding x-ray source angulation. The collimator is adjusted so as to adjust the x-ray beam to irradiate the reduced volume of interest of the breast, and after passing through the reduced volume of interest, irradiate the calculated detector area at each angulation. Thus, acquiring the third plurality of pre-fire projection images includes, at 236, adjusting collimator lateral and real blades at each angulation of the x-ray source based on the reduced volume of interest and the corresponding x-ray source angulation.

Continuing on to 240, the method 200 includes reconstructing the acquired pre-fire projection images to obtain a plurality of DBT pre-fire images. The plurality of DBT pre-fire images may be displayed on the user interface.

The plurality of pre-fire images may be used to confirm the position of the biopsy needle. Upon confirmation of the biopsy needle position (e.g., confirmation by the user) a biopsy gun may be deployed to fire the biopsy needle and collect biopsy samples. Subsequently, a biopsy clip may be inserted at or near the biopsy site to mark the biopsy location, and future monitoring.

Accordingly, the method 200 may confirm, at 242, if the needle has fired. Additionally or alternatively, the method 200 may confirm if the biopsy clip is inserted. The confirmation of needle firing and/or the confirmation of biopsy clip insertion may be based on user indication, for example. If the answer at 242 is NO, the method 200 may continue to monitor for confirmation of needle firing and/or post-fire clip insertion. If the answer at 242 is YES, the method 200 proceeds to 244.

At 244, the method 200 includes acquiring a fifth plurality of post-fire DBT projection images and/or post-clip projection images. In one example, during acquisition of the plurality of post-fire and/or post-clip projection images, the collimation may be adjusted based on the collimation applied during the acquisition of the pre-fire images. Said another way, the detector area to irradiate (that is the detector field of view (FOV)) during the post-fire acquisitions may be adjusted in the same manner as the pre-fire acquisitions. For example, if second larger field of view was applied during the pre-fire acquisitions, the plurality of post-fire and/or post-clip projections may be acquired with the dynamic detector collimation applied to irradiate the second larger volume of interest s(e.g., as discussed at steps 228 and 230). If the second narrower field of view was requested during the pre-fire acquisitions, the plurality of post-fire and/or post-fire projections may be acquired with the dynamic detector collimation applied to irradiate the reduced volume of interest that was used during pre-fire acquisitions (as discussed at steps 234 and 236)

Accordingly, acquiring fifth plurality of post-fire and/or post-clip DBT projection images includes, at 245, adjusting collimation based on the collimation applied during the pre-fire DBT acquisitions, which includes, at 246, adjusting one or more of the lateral and rear blade positions to obtain detector FOV (larger or narrower) implemented during the pre-fire DBT acquisitions. In some examples, the user may choose to use a third larger field of view for post-fire and/or post-clip acquisitions. Thus, the controller may provide the user with the option to choose a desired field of view (and thus, image a desired volume) at any workflow step.

Next, at 248, the method 200 includes reconstructing the post-fire and/or post-clip projection images to obtain a plurality of post-fire and/or post-clip DBT images, and displaying the post-fire and/or post-clip projection images on the user interface.

In this way, dynamic adjustment of collimation allows for reduced radiation exposure to the patient in one or more post target selection steps as the imaged area is reduced to the reduced volume of interest. Further, for one or more biopsy steps following target selection, a plurality of metallic objects (e.g., biopsy device parts) may be present in the vicinity of the compressed breast. By limiting the imaged portion to the reduced volume of interest, imaging artifacts due to the images capturing the metallic objects are reduced. Further, during DBT guided biopsy, a time to display the volume images (that is, time to reconstruct) is an important factor as the user is waiting for the images to be displayed before proceeding to the next step. By limiting the irradiation to the reduced volume of interest, the time to reconstruct post target selection is reduced.

Next, FIGS. 3A-3C show example schematic illustrations of dynamic collimation adjustment during DBT acquisitions after a biopsy target is selected. As discussed above, dynamic collimation adjustment includes adjusting collimator blade positions, including one or more of lateral and rear blade positions, to adjust a corresponding detector area irradiated for each angulation of the x-ray source during the DBT acquisitions. Upon selection of the biopsy target, the controller may determine, for each angulation, the corresponding detector area to irradiate, based on the volume of interest encompassing the biopsy target. The controller may then determine a corresponding collimator position for each angulation so as to irradiate the reduced volume of interest, and such that after the collimated beam passes through the reduced volume of interest, the corresponding detector area is irradiated. The controller may then adjust the collimator to the corresponding collimator position at each angulation to output an x-ray beam with a corresponding cone angle.

Turning to FIG. 3A, it shows a schematic illustration of a portion 300 of an x-ray system. The illustration shows a compressed breast 320 between a compression paddle 310 and a detector 315. Specifically, chest wall side of the detector 315 is shown. Further, the chest wall to nipple direction is the direction of the y-axis; the lateral direction 317 is the direction of x-axis; and the direction perpendicular to the x-axis and the y-axis upwards from the detector 315 to the compression paddle 310 is the direction of z-axis.

During DBT acquisition, x-ray source 305 may rotate from $-\alpha$ to $+\alpha$ about a center of rotation (not shown). A vertical axis 319 of the x-ray source passes through center of the rotation, and a medial position of the x-ray source 305 when the vertical axis 319 is perpendicular to the detection surface (that is, x-y plane) is referred to as the zero degree position (indicated by $\alpha 0$), and the x-ray source may rotate up to $-\alpha$ degrees on one side and up to $+\alpha$ degree on the other side of the medial position. Thus, an angular range of the x-ray source is from $-\alpha$ degree to $+\alpha$ degree. Various angulations (that is, plurality of angular positions of the x-ray source at which DBT acquisitions are obtained) of the x-ray source 305 within the angular range are also depicted in this illustration.

A volume of interest 322 within the compressed breast 320 is the reduced volume of interest, and is determined based on the target location selected by the user, breast thickness, and one or more compression paddle parameters, such as aperture area and location on the compression paddle. During DBT acquisition after the biopsy target is selected, the x-ray source is rotated within the angular range (between $-\alpha$ and $+\alpha$), and the volume of interest (322) is scanned at the plurality of angles within the angular range to obtain a plurality of projection images at the detector. The collimation at the plurality of angles are adjusted such that the detector area to irradiate is based on the volume of interest. Specifically, the collimation at the plurality of angles is adjusted by changing collimation at each of the plurality of angles. Thus, for each of the plurality of angles, the corresponding area to irradiate on the detector is computed based on the volume of interest and the angular position of the x-ray source. Based on the calculated area to irradiate, the collimation is adjusted by varying a cone angle of x-ray cone beam (depicted by dashed lines) by adjusting one or more of lateral blades and rear blades of the collimator. As an example, for each angular position of the x-ray source, including angulations $-\alpha 4, -\alpha 3, -\alpha 2, -\alpha 1, \alpha 0, +\alpha 1, +\alpha 2, +\alpha 3,$ and $+\alpha 4$, where $\alpha 0$ is the medial position of the x-ray tube, the detector area to irradiate may be calculated as follows:

$$Ai = f(V, \pm \alpha j, \alpha 0)$$

where i=1, 2, 3, ... n, n is the number of angular positions of the x-ray tube at which the reduced volume of interest (V) is scanned during DBT, ±represents the direction of the x-ray tube from the medial position $\alpha 0$, and j=1, 2, 3 ... ((n-1)/2).

Further, based on the area to irradiate, $\theta i$ may be determined, where $\theta$ is the cone angle of the x-ray beam output from the collimator and i=1, 2, 3, ... n. Thus, cone angle of the x-ray beam $\theta i$ corresponds to detector area to irradiate Ai.

The present example illustrates collimation adjustment in the lateral direction (that is, in the positive and negative directions of the x-axis). As illustrated, the collimated x-ray beam at each angle is limited to irradiate the volume of interest 322.

In this way, by adjusting collimation to limit radiation to the reduced volume of interest and based on angular position of x-ray source, imaging artifacts outside of the volume of interest may be reduced and an amount of radiation to the patient may be reduced while improving image quality and resolution.

Exemplary illustrations of rear collimation at the medial position of the x-ray source 305 for different breast thickness are shown at FIGS. 3B and 3C. Specifically, FIG. 3B shows collimation for a smaller breast thickness 330 in the portion 300 of the x-ray system, and FIG. 3C shows collimation for a greater breast thickness 340 in the portion 300 of the x-ray system. The volume of interest increases with increase in breast thickness. Thus, volume of interest 326 (FIG. 3C) is greater than volume of interest 324 (FIG. 3B). As a result, the area to irradiate also increases with increase in breast thickness. In order to scan a larger volume of interest, the collimation is adjusted to increase cone angle of the collimated x-ray beam. Thus, cone angle $\theta 11$ (FIG. 3C) is greater than cone angle $\theta 10$ (FIG. 3B). While the present examples at FIGS. 3B and 3C are illustrated for a single position of the x-ray source 305, it will be appreciated that corresponding adjustments in collimation may be made for each of the plurality of angulations of the x-ray source 305.

Next, a schematic illustration of collimation that may be applied for DBT acquisitions prior to target selection is shown at FIG. 3D. Specifically, a larger volume of interest is imaged prior to target selection. In one example, the larger volume of interest may include the entire breast in order to identify cancerous areas and localize a target tissue for biopsy or a target region of interest for diagnostic purposes. As the x-ray source 305 is rotated within the angular range, the detector area irradiated is changed at each angle and is greater than the detector areas irradiated during DBT acquisition after target selection when reduced volume is irradiated. In one example, prior to target selection, the cone angle at each angulation may be adjusted by adjusting one or more of lateral and rear collimator blades such that the detector area irradiated is changed to image the larger volume at each x-ray source angulation. Thus, each of cone angles $\theta 1, \theta 2, \theta 3 \ldots \theta 9$, may be adjusted such that the x-ray beam at each angulation irradiates a corresponding area on the detector after passing through the volume of interest of breast. In one example, each of cone angles $\theta 1, \theta 2, \theta 3 \ldots \theta 9$, may be different such that the x-ray beam at each angulation irradiates a different area on the detector after passing through the volume of interest of the breast. Taken together, prior to target selection, the cone angle of the x-ray beam at each angulation is determined based on covering a greater volume of the compressed breast, and thus a greater irradiated area on the detector in order to enable target selection.

In another example, prior to target selection, corresponding cone angles at a plurality of angulations of the x-ray source may be adjusted by adjusting one or more of lateral and rear collimator blades such that the detector area irradiated is adjusted to image the larger volume at each x-ray source angulation. Thus, each of plurality of cone angles of the x-ray beam may be adjusted such that the collimated x-ray beam at each angulation is limited to irradiate the larger volume of interest. As a result, the corresponding irradiated area on the detector after passing through the volume of interest of the breast is adjusted based on the x-ray tube angulation and the volume of interest.

Next, FIGS. 4A-4C show three-dimensional illustrations of a reduced volume of interest of a breast compressed between a compression paddle 410 and a detector 415, and further shows for different angular positions of the x-ray tube during DBT acquisition after target selection, a corresponding irradiated detection area on the detector 415. Further, FIGS. 4A-4C illustrate collimated x-ray fields 406 (also referred to as collimated rays) and projection of the reduced volume of interest on the detector in a lateral direction (direction of x-axis).

Turning to FIG. 4A, it shows a portion 400 of an x-ray system, such as the x-ray system of FIG. 1A, at a first angulation of the x-ray source wherein the x-ray source rotated clockwise to the first angulation with respect to the medial position (when the vertical axis of the x-ray source is perpendicular to the detection surface).

A volume of interest 422 is the reduced volume of interest and is shaded in grey for clarity purposes. The volume of interest 422 is determined, by an x-ray system controller, based on a target location selected by the user, a breast thickness, and one or more compression paddle parameters (e.g., aperture size and location on the paddle). Upon determining the volume of interest 422, the controller may determine an amount of opening of one or more of lateral and real collimator blades such that a collimated x-ray beam irradiates a detector area 407 (indicated by diagonal hatching) after passing through the volume of interest 422. In this figure, lateral collimator rays 406 are shown. It will be appreciated that, additionally, rear collimator blades may be adjusted to provide the desired collimation. Collimator blades 405 are adjusted such that a plurality of collimated rays 406 of the collimated x-ray beam pass through the volume of interest 422. Specifically, the plurality of collimated rays 406 may be the outermost collimated rays 406, and pass through each corner (each upper corner P, Q, R, and S, and each lower corner L, M, N, and O) of the cuboidal volume of interest 422. While the present examples illustrate few collimated rays 406, it will be appreciated that additional outermost collimated rays and a plurality of additional collimated rays passing through the volume of interest are part of the collimated x-ray beam. Further, while the present example shows a cuboidal volume of interest, other geometrical volumes, such as cubical volume, are also within the scope of the disclosure, and may be based on the type of collimator used. In any case, the outermost collimated rays of the collimated x-ray beam may pass through each of the outermost corners of the volume of interest (including the margin volume) before irradiating the detection area of the detector. Thus, the detection area 407 irradiated by the collimated x-ray beam is based on the volume of interest 422. The detection area 407 irradiated by the collimated x-ray beam is further based on the angulation of the x-ray source and the location of volume of interest. For example, when a smallest detector area is irradiated at the medial position, as the angulation of the x-ray source from the medial position increases, the detection area irradiated on the detector increases in either direction such that the irradiation by the collimated x-ray beam is limited to the volume of interest.

Next, FIG. 4B shows the portion 400 of the x-ray system at a second angulation of the x-ray source. Specifically, FIG. 4B shows the portion 400 when x-ray source at the medial position, wherein a vertical axis of the x-ray source is perpendicular to the detection surface of the detector 415. When the x-ray source is at the medial position, the collimator is commanded to adjust the amount of opening of the collimator such that collimated x-ray beam irradiates the volume of interest 422. As discussed above, collimation is adjusted such that the outermost collimated rays 406 pass through each of the corners of the cuboidal volume 422, and irradiate the detection area 427.

FIG. 4C shows the portion 400 of the x-ray system at a third angulation of the x-ray source, wherein the x-ray source is rotated anticlockwise such that the vertical axis of the x-ray source is at the third different angulation from the medial position. For each of the angulations of the x-ray tube, a corresponding irradiated detection area may be adjusted based on the volume of interest 422 and the x-ray tube angulation. For example, irradiated area 407 at FIG. 4A (first angulation), is different from irradiated area 427 at FIG. 4B (second angulation), and the irradiated area 457 at FIG. 4C (third angulation).

Taken together, when the irradiated detection area on the detector is minimum at a minimum angulation of the x-ray source (that is, 0 degree angulation when the x-ray source is at the medial position), the irradiated detection area increases with increase in x-ray tube angulation for x-ray tube rotations in either direction (clockwise and anti-clockwise) within the angular range of the x-ray source rotation, and depends on the direction of rotation. Further, for any x-ray source angulation, the outermost collimated rays may pass through the volume of interest (including the margin volume) such that each corner of the cuboidal volume of interest is irradiated by at least one collimated ray 406 of the collimated beam.

In this way, by collimating x-ray beam based on the x-ray source angulation (e.g., amount of angulation and direction of rotation) and the volume of interest that is based on selected target coordinates, breast thickness, and one or more compression paddle parameters, only a selected portion of the compressed breast is irradiated. This significantly reduces imaging artifacts as the acquisition is focused on the volume of interest. Further, as the irradiated detection area is adjusted based on the volume of interest, an overall amount of radiation that the patient receives is less. Furthermore, spatial resolution is improved.

An exemplary illustration of artifact reduction is shown at FIG. 9. Turning next to FIG. 9, it shows an exemplary scan image 900 of an image plane during a DBT acquisition obtained without applying dynamic collimation adjustment (that is, detection area irradiated remains the same for all x-ray source angulation) and an exemplary scan image 920 of the image plane obtained by adjusting collimation to irradiate detection area based on the volume of interest and angular position are shown. As illustrated, imaging artifacts, indicated by 910 on the scan image 900 and by 930 on the scan image 920, are reduced when collimation is adjusted based on the volume of interest and angular position of the x-ray source.

Further, as the breast thickness decreases, the area to irradiate decreases for the same angular positions of the x-ray source as illustrated in FIGS. 5A-5C. Specifically, FIGS. 5A-5C show three-dimensional illustrations of the portion 400 of the x-ray system depicting a second volume of interest and corresponding detector area to irradiate for a smaller breast thickness (compared to FIGS. 4A-4C) at different angular positions of the x-ray tube during DBT acquisition after target selection. As the thickness of the breast reduces, the volume of interest decreases. Thus, for the same angulation of the x-ray source, a volume of interest 522 is smaller for smaller breast compressed thickness. Consequently, a corresponding irradiated detection area on the detector 415 is smaller. For brevity and illustration purposes, FIGS. 5A-5C, the collimator portion is not shown, however it will be appreciated that a plurality of collimated rays 506 are output from a collimator, such as collimator 405 shown at FIGS. 4A-4C. Further, the plurality of collimated rays 506 may be outermost collimated rays of a collimated x-ray beam.

FIG. 5A shows the portion 400 with the x-ray source at the first angulation, FIG. 5B shows the portion 400 with the x-ray source at the second angulation, and FIG. 5C shows the portion 400 with the x-ray source at the third angulation. Further, as discussed above, FIGS. 5A-5C illustrate the volume of interest 522 for smaller compressed breast thickness (that is, distance in the z direction between the detection surface 415 and the compression paddle 410 is z=50 mm), while FIGS. 4A-4C illustrate the volume of interest 422 for greater compressed breast thickness (z=100 mm) for the first, second, and third angulations of the x-ray source. Thus, for the first angulation, an irradiated area 507 is smaller than the irradiated area 407. Similarly, for the second angulation, an irradiated area 527 is smaller than the irradiated area 427; and for the third angulation, an irradiated area 557 is smaller than the irradiated area 457. Thus, for smaller breast thickness (z distance reduced), a corresponding irradiated area on the detector is reduced as the projection of volume of interest on the detection surface decreases in the lateral direction (direction of x-axis). Further, an area to irradiate in the chest wall to nipple direction (direction of y-axis) is also reduced for smaller breasts. A three-dimensional illustration of the volume of interest 522 with the x-ray source at the second angulation and corresponding irradiated detection area 627 in the chest wall to nipple direction is shown at FIG. 6.

As discussed above, the collimation is adjusted such that at least one or more of the outermost collimated rays 506 pass through each corner of the cuboidal volume of interest 522.

Turning to FIG. 6, a three dimensional illustration depicting rear collimation after target selection for the portion 400 of the x-ray system at zero degree angulation of the x-ray source (that is, medial position of the x-ray source) is shown. Specifically, irradiated detection area 627 in the x-y plane corresponding to the projection of the volume of interest 522 for smaller breast thickness (distance in the z direction between the detection surface 415 and the compression paddle 410 is z=50 mm) is shown. The irradiated detection area 627 is reduced in a chest wall to nipple direction (direction of y-axis from a chest side 602 to nipple side 604) for smaller compressed breast thickness. Further, the irradiated detection area 627 is reduced with respect to an irradiated detection area (at the same x-ray source angulation) prior to target selection.

While the above embodiments described at FIGS. 2A-6, illustrate dynamic collimation by changing irradiated detection area at each x-ray source angulation during DBT acquisition, the dynamic collimation may be implemented for other mammography modes including stereo mammography or CESM mammography imaging as described below.

Figure 7:
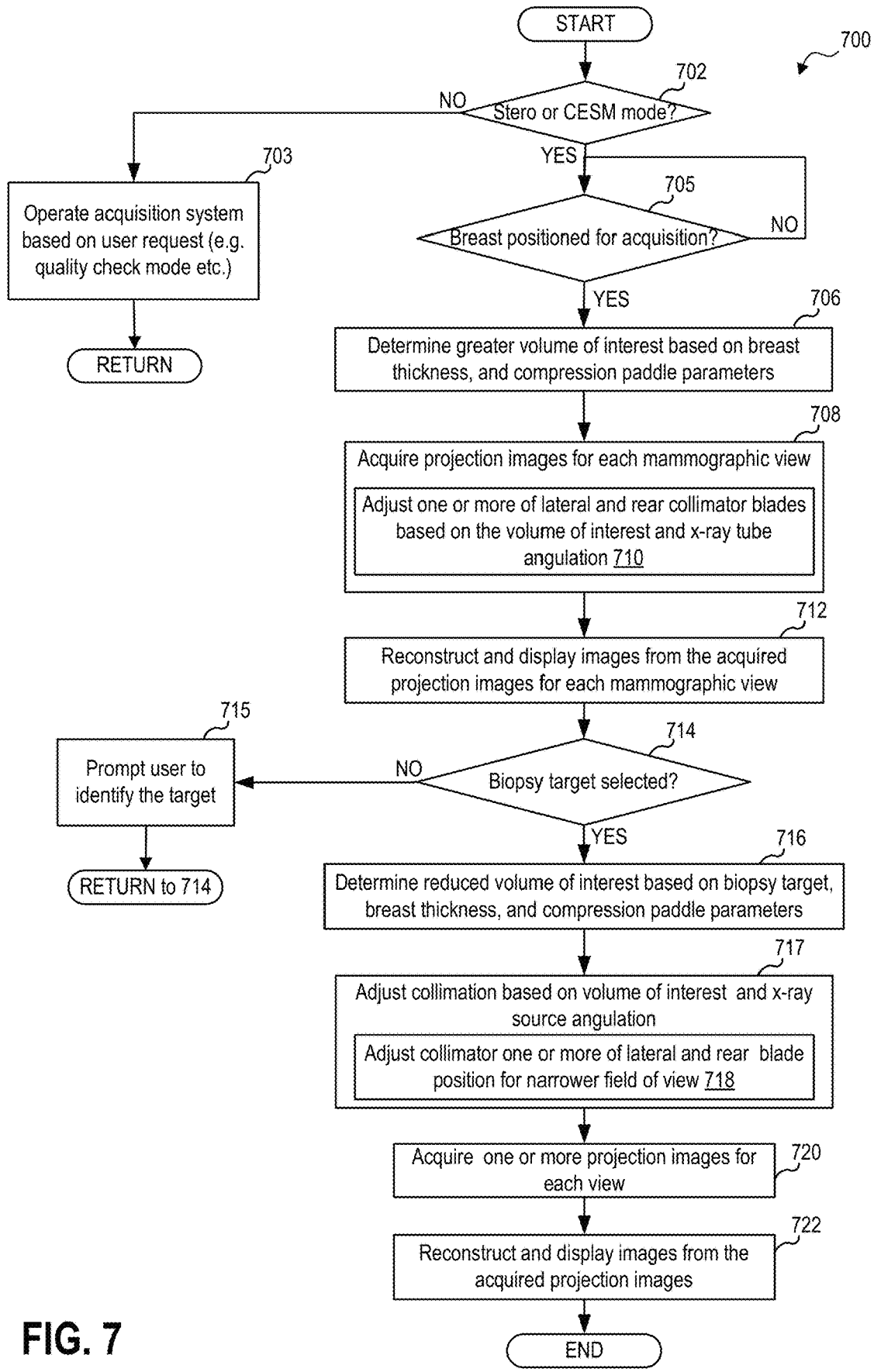
FIG. 7 is a high-level flow chart illustrating a method for performing dynamic collimation during one or more a stereo-guided biopsy and a CESM-guided biopsy; according to an embodiment of the disclosure.
Figure 8:
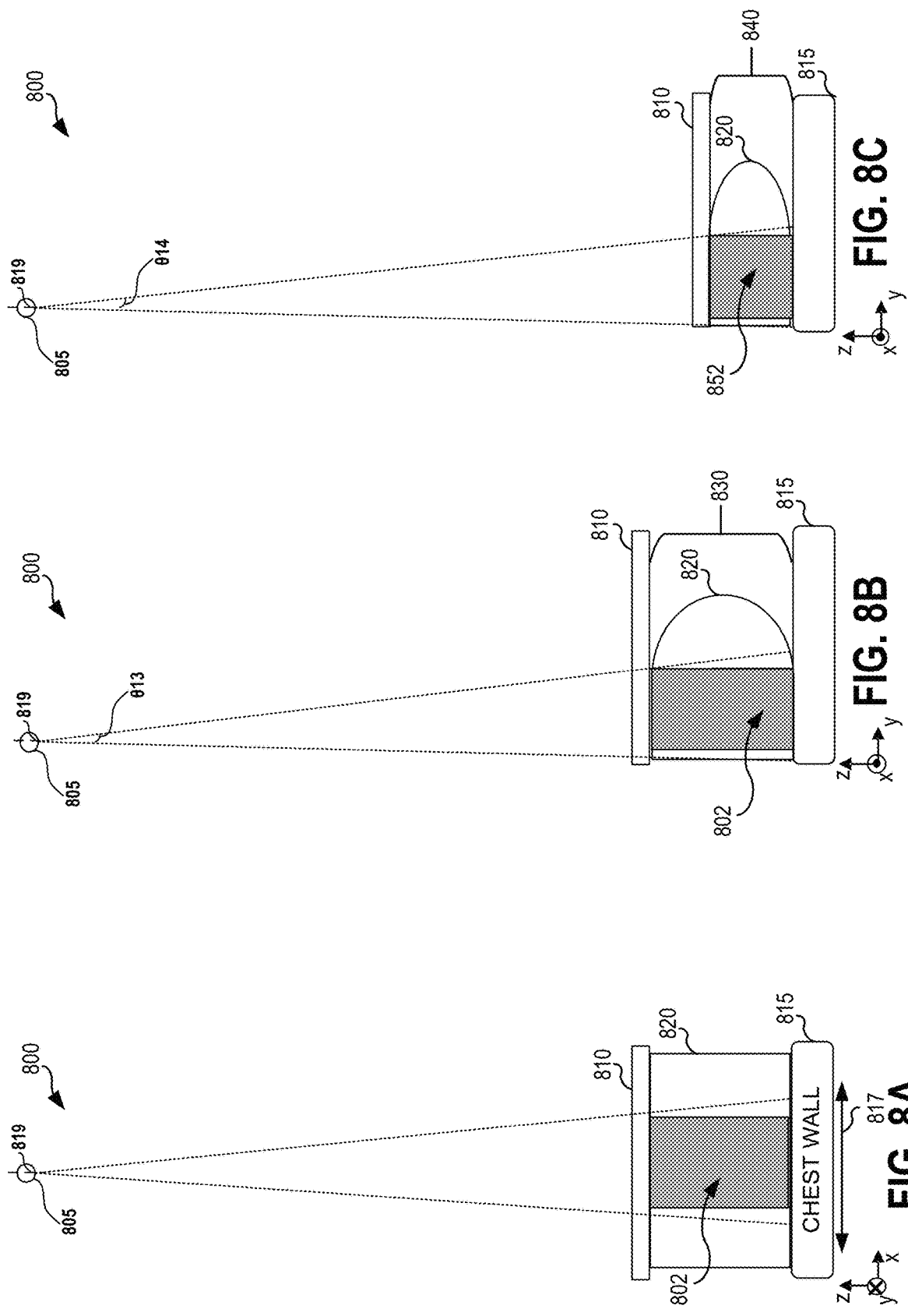
FIG. 8A is a schematic illustration of dynamic lateral collimation during one or more a stereo-guided biopsy and a CESM-guided biopsy, according to an embodiment of the disclosure.
FIG. 8B is a schematic illustration of dynamic rear collimation during one or more a stereo-guided biopsy and a CESM-guided biopsy, according to an embodiment of the disclosure.
FIG. 8C is another schematic illustration of dynamic rear collimation during one or more a stereo-guided biopsy and a CESM-guided biopsy, according to an embodiment of the disclosure.

FIG. 7 shows a flow chart illustrating a high-level method 700 for dynamic collimation that may be utilized during stereo-guided biopsy or CESM guided biopsy with an x-ray imaging system, such as x-ray system 10 at FIG. 1A, and a biopsy device, such as biopsy device 140 at FIG. 1B. The method 700 may be implemented by an image processing system, such as controller 44 at FIG. 1A, an edge device connected to the image processing system, a cloud in communication with the image processing system, or any appropriate combination thereof. The method 700 is described with regard to the systems and components of FIG. 1A, although it should be appreciated that the method 700 may be implemented with other systems and components without departing from the scope of the present disclosure.

The method 700 begins at 702. At 702, the method 700 includes confirming if the x-ray system is operated in a stereo-guided biopsy or CESM-guided biopsy mode. In one example, the mode of operation of the x-ray system may be determined based on an indication from a user on a user interface of the x-ray system. For example, the controller may determine the mode of operation based on the user launching an application interface corresponding to the mode of operation (e.g., launching a stereo or CESM interface). Other embodiments where a vision system coupled to the x-ray system is utilized to determine the mode of operation (based on accessory detection with the vision system, for example) are also within the scope of the disclosure.

If stereo or CESM guided biopsy mode is not confirmed, the method proceeds to 703 to operate the x-ray system based on user request mode (e.g., a quality check mode). Method 700 then ends. If stereo mode or CESM mode is confirmed, method 700 proceeds to 705. At 705, the method 700 includes confirming if the breast is positioned for biopsy. Step 705 is similar to step 204 at FIG. 2A, and will not be repeated for brevity. If breast positioning for stereo or CESM biopsy is confirmed, method 700 proceeds to 706; otherwise, the method 700 may continue to monitor for breast positioning confirmation.

At 706, the method 700 includes determining a volume of interest based on breast thickness, and compression paddle parameters. Specifically, the volume of interest may include a greater portion of the compressed breast prior to target selection, as discussed above with respect to DBT-guided biopsy.

Upon determining the volume of interest, the method 700 proceeds to 708. At 708, the method 700 includes acquiring one or more projection images for each mammographic view. The mammographic view may be based on the mode of operation. Specifically, when operating in the CESM-guided biopsy mode, the mammographic view may include one or more of CC view and MLO view. It will be appreciated that breast may be re-positioned between acquisitions for each view. Further, when operating in the CESM-guided mode, at least two projection images may be obtained. Specifically, a low energy acquisition and a high energy acquisition (after intravenous administration of an iodinated contrast agent) for each view may be obtained.

When operating in the stereo guided biopsy mode, at least two angulated views (for example, at +15 degrees and −15 degrees) may be obtained. Further, in the stereo-guided mode, a CC view (zero degree angulation of the x-ray source) may be obtained.

Acquiring one or more projection images for each view includes, at 710, adjusting one or more of the lateral and rear collimator blades to provide collimation based on the greater volume of interest prior to target selection. For each view, one or more projection image may be obtained with the collimator adjusted to irradiate the greater breast volume, and as such, a corresponding detection area on the detector irradiated is greater prior to target selection. Further, for a given mode, the irradiated detection area may be adjusted based on the x-ray tube position each view. For example, when operating in the CESM-guided mode, for each of the CC view and the MLO view, the corresponding detection area irradiated may be based on the x-ray tube angulation at the CC view and the MLO view. When operating in the stereo mode, for each stereo view and for the CC view at zero degrees, the corresponding detection area irradiated may be adjusted based on angulation of the x-ray tube at each view (stereo view angulation and CC view angulation).

Continuing on to 712, the projection images may be reconstructed and displayed to the user for each mammographic view.

Based on the reconstructed images, the user may select a target location, via the user interface, for example. Accordingly, the method 700 then proceeds to 714 to determine if the target location is selected. The target location may be within a region of interest and may be selected by the user, via the x-ray system user interface and/or the biopsy tool interface, based on identification of an abnormality from the reconstructed images (e.g., from step 712).

If the target is not identified, the answer at 714 is NO, and the method 700 proceeds to 715. At 715, the controller may prompt user to identify the target, and the method may return to 714 to determine if the target has been selected.

If the target is identified by the user and/or received at the controller, the answer at 714 is YES, and the method 700 proceeds to 716.

At 716, the method 700 includes determining, a reduced volume of interest based on the target location, breast thickness, and one or more compression paddle parameters (e.g., biopsy aperture on the paddle). The reduced volume of interest determined after target selection is less than the greater volume of interest determined prior to target selection.

Next, at 717, the method 700 includes adjusting collimation based on the reduced volume of interest and corresponding x-ray source angulation for the corresponding view (e.g., zero degree for CC view, 45 degrees for MLO view, and desired angulation for stereo views). This includes, at 718, adjusting one or more of lateral and rear blade positions of the collimator so as to irradiate the reduced volume of interest with the collimated x-rays. Consequently, a corresponding detection area irradiated is reduced, resulting in a narrower detector field of view after target selection compared to the detection area irradiated prior to target select for the same x-ray source angulation.

Upon adjusting the collimator based on the reduced volume of interest and x-ray source angulation (based on the view), the method 700 proceeds to 720. At 720, the method 700 includes acquiring one or more projection images for each view with the collimation adjusted for the reduced volume of interest and narrower detector field of view.

Continuing on to 722, the method 700 includes reconstructing the one or more projection images for each view, and displaying the reconstructed images to the user on the user interface.

The method 700 then ends.

In this way, responsive to selecting the target, the collimator blade positions are commanded to provide collimated x-rays for the reduced volume of interest. Further, as discussed above with respect to DBT-guided biopsy, the reduced volume of interest may be based on the breast thickness. For example, for greater compressed breast thickness, the reduced volume of interest is greater, and decreases with decrease in compressed breast thickness.

It will be appreciated that the adjustment of collimation may be implemented for one or more imaging procedures performed with the x-ray mammography system. The imaging procedures may include one or more of diagnostic and screening imaging procedures in addition to image-guided interventional procedures described above. For example, during the one or more of diagnostic and screening procedures, the user may select a region of interest and a reduced volume based on the region of interest may be determined by the controller. The collimator may then be adjusted to irradiate the reduced volume including the region of interest. The one or more of diagnostic and screening imaging procedures may include 2D screening procedure, 2D diagnostic procedure, DBT screening procedure, DBT diagnostic procedure, and CESM diagnostic procedure.

Exemplary collimation adjustment based on the reduced volume of interest for stereo guided biopsy and CESM guided biopsy modes is illustrated below with respect to FIGS. 8A, 8B, and 8C.

Turning to FIGS. 8A, 8B, and 8C, each show a portion 800 of an x-ray system, such as the x-ray system of FIG. 1A. Specifically, an x-ray source 805 is shown at a medial angulation (zero degree angulation) wherein a vertical axis 819 of the x-ray source is perpendicular to a detection surface of a detector 915. Turning to FIG. 8A, collimation of x-ray beam, indicated by dashed lines, in a lateral direction 817 (that is, the direction of x-axis) is shown. Upon selection of biopsy target, the collimation is adjusted to irradiate a reduced volume of interest 802 of the breast 820 compressed between a compression paddle 810 and the detector 815. Specifically, collimation is adjusted such that the irradiation by the collimated x-ray beam is limited to the reduced volume, and as a result, the detection area irradiated on the detection surface is reduced after the target is selected. Further, the detection area irradiated on the detection surface is based on the x-ray source angulation. For example, as the x-ray source angulation increases, a corresponding detection area irradiated by the collimated beam after passing through the reduced volume of interest also increases. As discussed above, the reduced volume of interest 802 is determined based on the selected biopsy target coordinates, compressed breast thickness, and one or more compression paddle parameters.

Further, exemplary illustrations of rear collimation (the direction of y-axis from chest wall to nipple) at the medial position of the x-ray source 805 for different breast thickness are shown at FIGS. 8B and 8C. Specifically, FIG. 8B shows collimation for a smaller breast thickness 830, and FIG. 8C shows collimation for a greater breast thickness 840. The volume of interest increases with increase in breast thickness. Thus, volume of interest 852 (FIG. 8C) is greater than volume of interest 802 (FIG. 8B). As a result, the area to irradiate also increases with increase in breast thickness. In order to scan a larger volume of interest, the collimation is adjusted to increase cone angle of the collimated x-ray beam. Thus, cone angle θ14 (FIG. 8C) is greater than cone angle θ13 (FIG. 8B). While the present examples at FIGS. 8B and 8C are illustrated for a single position of the x-ray source 805, it will be appreciated that corresponding adjustments in collimation may be made for each of the desired angulations of the x-ray source 805.

The technical effect of adjusting detection area irradiated based on a volume of interest during acquisitions after target selection is reduced imaging artifacts. Another technical effect of dynamically changing the detection area irradiated during acquisitions after target selection is reduced reconstruction time. Yet another technical effect of dynamically changing detection area after target selection is improved spatial resolution of the volume of interest.

An embodiment for an x-ray system comprises: during an imaging procedure performed with the x-ray system, adjusting collimation to image a corresponding volume of interest based on a workflow step of the imaging procedure. A first example of the method includes wherein adjusting collimation includes during a first positioning acquisition prior to selecting a target region of interest, irradiating a first larger area on a detector of the x-ray system based on a first volume of interest. In a second example of the method, which optionally includes the first example, the method further includes wherein adjusting collimation includes responsive to selecting the target region of interest, irradiating a second smaller area on the detector based on a second volume of interest; and wherein the first volume of interest is greater than the second volume of interest. In a third example of the method, which optionally includes one or both of the first and second examples, the method further includes wherein the first larger area and the second smaller area are further based on an angular position of the x-ray source of the x-ray system. In a fourth example of the method, which optionally includes one or more of each of the first through third examples, the method further includes wherein the second volume of interest is determined based on the selected region of interest, compressed breast thickness, and one or more compression paddle parameters. In a fifth example of the method, which optionally includes one or more of each of the first through fourth examples, the method further includes wherein the one or more compression paddle parameters includes a size and location of a compression paddle aperture. In a sixth example of the method, which optionally includes one or more of each of the first through fifth examples, the method includes during a digital breast tomosynthesis (DBT) acquisition, for each angular position of the x-ray source, responsive to selecting the target region of interest, adjusting collimation based on the second volume of interest and a corresponding angular position of the x-ray source. In a seventh example of the method, which optionally includes one or more of each of the first through sixth examples, the method includes wherein adjusting collimation based on the second volume of interest and the corresponding angular position of the x-ray source includes adjusting one or more collimator blade positions at each angular position of the x-ray source. In an eighth example of the method, which optionally includes one or more of each of the first through seventh examples, the method includes wherein adjusting collimation based on the second volume of interest and the corresponding angular position of the x-ray source includes changing the area to irradiate at each angular position of the x-ray source. In a ninth example of the method, which optionally includes one or more of each of the first through eighth examples, the method includes during the DBT acquisition, prior to selecting the target region of interest, adjusting collimation based on the first volume of interest and the corresponding angular position of the x-ray source.

An embodiment of a method for an x-ray system, comprises: during an image-guided interventional procedure, prior to selecting a target, performing a first tomosynthesis scan of a compressed breast with first collimation at a plurality of angular positions of an x-ray source of the x-ray system; reconstructing a first set of images from first tomosynthesis scan data; responsive to target selection from the first set of images, performing a second tomosynthesis scan of the compressed breast with second collimation at the plurality of angular positions of the x-ray system; and reconstructing a second set of images from first tomosynthesis scan data; wherein the first collimation is based on a greater volume of interest; and wherein the second collimation is based on a reduced volume of interest. A first example of the method includes wherein the first collimation is based on a corresponding x-ray source angulation, and is adjusted to irradiate a corresponding greater area on a detector of the x-ray system at each of the plurality of angular positions; wherein the second collimation is based on the corresponding x-ray source angulation, and is adjusted to irradiate a corresponding reduced area on the detector at each of the plurality of angular positions. In a second example of the method, which optionally includes the first example, and further includes wherein each of the greater area and the reduced area is changed at each angular position by adjusting one or more of lateral and rear collimator blade positions at each angular position; and wherein a first average detector area irradiated during the first tomosynthesis scan is greater than a second average detector area irradiated during the second tomosynthesis scan. In a third example of the method, which optionally includes one or both of the first and second examples, the method further includes when an interventional tool is in a pre-fire position, performing a pre-fire tomosynthesis scan of the compressed breast with the interventional tool in the pre-fire position with the second collimation; and reconstructing pre-fire images based on pre-fire scan data from the pre-fire tomosynthesis scan. In a fourth example of the method, which optionally includes one or more of each of the first through third examples, the method further includes wherein the reduced volume of interest is based on a position of the selected target, a compressed breast size, and one or more compression paddle parameters. In a fifth example of the method, which optionally includes one or more of each of the first through fourth examples, the method further includes wherein the image guided interventional procedure is an image guided biopsy procedure. In a sixth example of the method, which optionally includes one or more of each of the first through fifth examples, the method includes wherein the volume of interest increases with increase in compressed breast thickness; and wherein the compression paddle parameters includes a compression paddle aperture size and location.

An embodiment for an imaging system is provided. The imaging system comprises a radiation source rotating within an angular range about an axis of the imaging system; a collimator to adjust emission of radiation from the radiation source; a detector for receiving radiation rays from the radiation source via the collimator and generating a plurality of projection images of a specimen positioned between the radiation source and the detector; a compression paddle for positioning the specimen between the compression paddle and the detector; a biopsy device including a biopsy tool and a biopsy needle mounted on the biopsy tool, the biopsy device coupled to the imaging system and positioned between the radiation source and the detector; and a processor with executable instructions stored in non-transitory memory for: prior to receiving biopsy target coordinates, adjusting one or more collimator blades to irradiate an area on the detector based on a whole volume of specimen, and performing a first tomosynthesis scan by adjusting one or more collimator blade positions at each angular position of the radiation source; reconstructing first set of images from the first tomosynthesis scan; displaying the first set of images on a user interface of the imaging system; responsive to receiving biopsy target coordinates, determining a reduced volume of interest based on the biopsy target coordinates, compressed breast thickness, and one or more compression paddle parameters; determining a corresponding area to irradiate on the detector based on the reduced volume of interest for each radiation source angular position; performing a second tomosynthesis scan by adjusting one or more collimator blades at each radiation source angular position based on the corresponding area to irradiate; reconstructing second set of images from the first tomosynthesis scan; and displaying the second set of images on the user interface. In a first example of the imaging system, the corresponding area to irradiate increases with increase in angulation of the radiation source with respect to a medial position at which a vertical axis of the radiation source is perpendicular to a detection surface of the detector. In a second example of the imaging system, which optionally includes the first example, adjusting one or more collimator blades includes adjusting one or more of lateral blades and rear blade positions.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an x-ray system, comprising:
during an imaging procedure performed with an x-ray source of the x-ray system in which the x-ray source is moved through a plurality of angular positions,
adjusting collimation based on an angular position of the x-ray source and a corresponding reduced volume of interest at each of the plurality of angular positions to reduce radiation during the imaging procedure and image the corresponding reduced volume of interest based on a workflow step of the imaging procedure,
wherein adjusting the collimation includes changing both a cone angle of an x-ray beam output by the x-ray source and a detector area at each of the plurality of angular positions based on the reduced volume of interest, and wherein the reduced volume of interest is determined based on estimated coordinates of a selected target, and
imaging the entire corresponding reduced volume of interest while excluding volume outside of the corresponding reduced volume of interest,
and wherein adjusting the collimation includes adjusting a collimator such that outermost collimated rays pass through each corner of the cuboidal volume of interest before irradiating the detector area at each of the plurality of angular positions.

2. The method of claim 1, wherein adjusting collimation includes, during a first positioning acquisition prior to selecting the selected target, irradiating a first larger area on a detector of the x-ray system based on a first volume of interest, and wherein irradiating the first larger area includes adjusting the cone angle at each of an initial plurality of angular positions so that a corresponding x-ray beam at each of the initial plurality of angular positions is limited to the first volume of interest.

3. The method of claim 2, wherein the corresponding reduced volume of interest is a second volume of interest, wherein the first volume of interest is greater than the second volume of interest, and wherein adjusting the collimation based on the angular position of the x-ray source and the corresponding reduced volume of interest at each of the plurality of angular positions limits irradiation to the reduced volume of interest.

4. The method of claim 3, wherein the second volume of interest is further determined based on a compressed breast thickness and one or more compression paddle parameters such that, for a same angulation of the plurality of angular positions, the reduced volume of interest is smaller for smaller breast compressed thickness.

5. The method of claim 4, wherein the one or more compression paddle parameters includes a size and location of a compression paddle aperture.

6. The method of claim 2, wherein the selected target is a user-selected target made from the first volume of interest that is already imaged via the x-ray system, and wherein the first volume of interest is greater than the reduced volume of interest.

7. The method of claim 1, wherein adjusting collimation based on the corresponding reduced volume of interest and the angular position of the x-ray source includes adjusting one or more of lateral and rear collimator blade positions of collimator blades at each of the plurality of angular positions of the x-ray source to adjust the cone angle of the x-ray beam output.

8. The method of claim 1, further comprising:
imaging an initial volume of interest prior to imaging the corresponding reduced volume of interest,
wherein the initial volume of interest is greater than the corresponding reduced volume of interest, and
wherein the adjusted collimation at each of the plurality of angular positions for imaging the corresponding reduced volume of interest has a narrower field of view than a field of view for imaging the initial volume of interest.

9. The method of claim 1, wherein the x-ray system automatically applies dynamic collimation for a greater field of view prior to selecting the selected target, and
wherein the x-ray system automatically switches to apply the adjusted collimation at each of the plurality of angular positions to image the corresponding reduced volume of interest with a narrower field of view after selecting the selected target.

10. The method of claim 1, wherein the x-ray source is a radiation source.

11. A method for an x-ray system, comprising:
during an image-guided interventional procedure,
prior to selecting a target, performing a first tomosynthesis scan of a compressed breast with first collimation at a plurality of angular positions of an x-ray source of the x-ray system;
reconstructing a first set of images from data of the first tomosynthesis scan;
responsive to a target selection from the first set of images, performing a second tomosynthesis scan of the compressed breast with second collimation at the plurality of angular positions of the x-ray system; and
reconstructing a second set of images from data of the second tomosynthesis scan;
wherein the first collimation is based on a greater volume of interest;
wherein the second collimation is based on a reduced volume of interest, and
wherein a volume of the reduced volume of interest is less than the greater volume of interest;
wherein the second tomosynthesis scan includes adjusting the second collimation based on an angular position of the x-ray source and the reduced volume of interest at each of the plurality of angular positions to reduce radiation during the image-guided interventional procedure; and
wherein adjusting the second collimation includes changing both a cone angle of an x-ray beam output by the x-ray source and a detector area at each of the plurality of angular positions based on the reduced volume of interest, and wherein the reduced volume of interest determined is based on estimated coordinates of the target selected from the first set of images, and
imaging the entire reduced volume of interest while excluding volume outside of the reduced volume of interest,
wherein the reduced volume of interest is a cuboidal volume of interest, and wherein adjusting the second collimation includes adjusting a collimator such that outermost collimated rays pass through each corner of the cuboidal volume of interest before irradiating the detector area at each of the plurality of angular positions.

12. The method of claim 11, wherein the first collimation is further based on a corresponding x-ray source angulation and the first collimation is adjusted to irradiate a corresponding greater area on a detector of the x-ray system at each of the plurality of angular positions, and wherein the second collimation is further based on the corresponding x-ray source angulation and the second collimation is adjusted to irradiate a corresponding reduced area on the detector at each of the plurality of angular positions.

13. The method of claim 12, wherein each of the corresponding greater area and the corresponding reduced area is changed at each of the plurality of angular positions by adjusting one or more of lateral and rear collimator blade positions at each angular position, and wherein a first average detector area irradiated during the first tomosynthesis scan is greater than a second average detector area irradiated during the second tomosynthesis scan.

14. The method of claim 11, further comprising:
when an interventional tool is in a pre-fire position, performing a pre-fire tomosynthesis scan of the compressed breast with the interventional tool in the pre-fire position with the second collimation; and
reconstructing pre-fire images based on pre-fire scan data from the pre-fire tomosynthesis scan.

15. The method of claim 11, wherein the reduced volume of interest is based on the estimated coordinates of the target selected, a compressed breast size, and one or more compression paddle parameters.

16. The method of claim 15, wherein the reduced volume of interest increases in volume with an increase in compressed breast thickness, wherein a corresponding cone angle for irradiating the reduced volume of interest is increased with the increase in compressed breast thickness via the adjusted second collimation, and wherein the one or more compression paddle parameters includes a compression paddle aperture size and location.

17. An imaging system, comprising:
a radiation source rotating within an angular range about an axis of the imaging system;
a collimator to adjust emission of radiation from the radiation source;
a detector for receiving radiation rays from the radiation source via the collimator and generating a plurality of projection images of a specimen positioned between the radiation source and the detector;
a compression paddle for positioning the specimen between the compression paddle and the detector;
a biopsy device including a biopsy tool and a biopsy needle mounted on the biopsy tool, the biopsy device coupled to the imaging system and positioned between the radiation source and the detector; and
a processor with executable instructions stored in non-transitory memory for:
during an imaging procedure, prior to receiving biopsy target coordinates,
adjusting a collimation by adjusting one or more collimator blades to irradiate an area on the detector based on a whole volume of the specimen, and performing a first tomosynthesis scan by adjusting the one or more collimator blades at each of a plurality of angular positions of the radiation source;
reconstructing a first set of images from the first tomosynthesis scan; and
displaying the first set of images on a user interface of the imaging system; and
responsive to receiving the biopsy target coordinates,
determining a reduced volume of interest based on the biopsy target coordinates, compressed breast thickness, and one or more compression paddle parameters;
determining a corresponding area to irradiate on the detector based on the reduced volume of interest for each of the plurality of angular positions of the radiation source;
performing a second tomosynthesis scan by adjusting the one or more collimator blades at each of the plurality of angular positions of the radiation source based on the corresponding area to irradiate, wherein the adjusting of the one or more collimator blades is further based on the reduced volume of interest at each of the plurality of angular positions of the radiation source to reduce radiation during the imaging procedure, and wherein adjusting the one or more collimator blades includes changing both a cone angle of an x-ray beam output by the radiation source and a detector area that is irradiated by the radiation output by the radiation source at each of the plurality of angular positions based on the reduced volume of interest, and wherein the reduced volume of interest based on the biopsy target coordinates received, and imaging the entire reduced volume of interest while excluding volume outside of the reduced volume of interest;

reconstructing a second set of images from the second tomosynthesis scan; and displaying the second set of images on the user interface, wherein the reduced volume of interest is a cuboidal volume of interest, and wherein adjusting the collimation includes adjusting the collimator such that outermost collimated rays pass through each corner of the cuboidal volume of interest before irradiating the detector area at each of the plurality of angular positions.

18. The system of claim 17, wherein the corresponding area to irradiate increases with an increase in angulation of the radiation source with respect to a medial position at which a vertical axis of the radiation source is perpendicular to a detection surface of the detector.

19. The system of claim 17, wherein adjusting the one or more collimator blades includes adjusting both lateral and rear blade positions of the collimator to change the cone angle.

* * * * *